US011435365B2

(12) United States Patent
Yerramilli et al.

(10) Patent No.: US 11,435,365 B2
(45) Date of Patent: Sep. 6, 2022

(54) MARKERS FOR RENAL DISEASE

(71) Applicant: IDEXX Laboratories, Inc., Westbrook, ME (US)

(72) Inventors: Mahalakshmi Yerramilli, Falmouth, ME (US); Michael Randolph Atkinson, Gorham, ME (US); Murthy V. S. N. Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 16/571,345

(22) Filed: Sep. 16, 2019

(65) Prior Publication Data

US 2020/0049719 A1 Feb. 13, 2020

Related U.S. Application Data

(62) Division of application No. 13/700,992, filed as application No. PCT/US2011/039122 on Jun. 3, 2011, now Pat. No. 10,436,797.

(60) Provisional application No. 61/411,280, filed on Nov. 8, 2010, provisional application No. 61/351,183, filed on Jun. 3, 2010.

(51) Int. Cl.
*G01N 33/68* (2006.01)
*G01N 33/53* (2006.01)
*G01N 33/92* (2006.01)

(52) U.S. Cl.
CPC ..... *G01N 33/6893* (2013.01); *G01N 33/5308* (2013.01); *G01N 33/92* (2013.01); *G01N 2800/347* (2013.01); *G01N 2800/60* (2013.01)

(58) Field of Classification Search
None
See application file for complete search history.

(56) References Cited

U.S. PATENT DOCUMENTS

| 5,726,010 A | 3/1998 | Clark |
| 2007/0087448 A1 | 4/2007 | Nelsestuen |
| 2007/0105114 A1 | 5/2007 | Li et al. |
| 2007/0212738 A1 | 9/2007 | Haley et al. |
| 2008/0064047 A1 | 3/2008 | Zetter et al. |
| 2009/0023165 A1 | 1/2009 | Haigh et al. |
| 2010/0145398 A1 | 6/2010 | Li et al. |
| 2012/0003752 A1* | 1/2012 | Struck .................. G01N 33/74 436/501 |
| 2012/0329071 A1* | 12/2012 | Chance .............. G01N 33/6893 435/7.4 |
| 2018/0106817 A1 | 4/2018 | Chance et al. |

FOREIGN PATENT DOCUMENTS

| JP | 2003177125 A | 6/2003 |
| JP | 2009511913 A | 3/2009 |
| JP | 2010522871 A | 7/2010 |
| WO | 2003031967 A1 | 4/2003 |
| WO | 2004002518 A2 | 1/2004 |
| WO | 2004048598 A2 | 6/2004 |
| WO | 2005049806 A2 | 6/2005 |
| WO | 2006081473 A2 | 8/2006 |
| WO | 200713575 A2 | 2/2007 |
| WO | 2007044944 A2 | 4/2007 |
| WO | 2007047458 A2 | 4/2007 |
| WO | 2007070021 A1 | 6/2007 |
| WO | 2008021290 A2 | 2/2008 |
| WO | 2008116867 A1 | 10/2008 |
| WO | 2009136182 A1 | 11/2009 |
| WO | 2011079280 A2 | 6/2011 |
| WO | 2011109830 A2 | 9/2011 |
| WO | 2010126146 A | 11/2012 |

OTHER PUBLICATIONS

NKF KDOQI Guidelines, 1-9, retrieved from https://kidneyfoundation.cachefly.net/professionals/KDOQI/guideline_diabetes/guide5.htm on Jul. 1, 2021, 2007. (Year: 2007).*
Extended European Search Report in EP Application No. 21150480. 8-1110, dated Jun. 4, 2021, 8 pages.
Kamel et al, "Acid Cystine Proteinase Inhibitor (cystatin A) Differentiates Oncocytomas from Renal Cell Carcinomas", The Journal of Pathology; 176th Meeting of The Pathological Society of Great Britain and Ireland, vol. 184, p. 40A, Jan. 1, 1998.
Schaefer et al., "Urinary excretion of cathespin B cystatins as parameters of tubular damage", Kidney International, vol. 46, No. 7, pp. S-64-S-67, (1994).
Niwa et al., "RNA metabolism in uremic patients: Accumulation of modified ribonucleosides in uremic serum", Kidney International, 53:1801-1806 (1998).
Boudonck et al., "Discovery of Metabolomics Biomarkers for Early Detection of Nephrotoxicity", Toxicologi Pathology, 37:280-292 (2009).
Xia et al., "Correlations of six related purine metabolites and diabetic nephropathy in Chinese type 2 diabetic patients", Clinical Biochemistry, 42:215-220 (2009).
Mansell et al., "Effect of renal failure on erythrocyte purine nucleotide, nucleoside and base concentrations and some related enzyme activities", Clinical Science, 61:757-764 (1981).
Xia et al., "Ultraviolet and tandem mass spectrometry for simultaneous quantification of 21 pivotal metabolites in plasma from patients with diabetic nephropathy", Journal of Chromatography B, 87:1930-1936 (2009).

(Continued)

Primary Examiner — Changhwa J Cheu
(74) Attorney, Agent, or Firm — DLA Piper LLP US

(57) ABSTRACT

This invention provides reagents and methods for diagnosing renal disease. Differential levels of inosine metabolite, and proteins: apolipoprotein C-I, apolipoprotein C-II, fibrinogen alpha chain, or fibrinogen A-alpha chain, kininogen, Inter-Alpha Inhibitor H4 (ITIH4), keratin Type I cytoskeletol 10 cystatin A, cystatin B and other polypeptides and fragments thereof provide biomarkers of renal disease and are described herein.

9 Claims, 4 Drawing Sheets

Specification includes a Sequence Listing.

(56) References Cited

OTHER PUBLICATIONS

Jornen et al., "Detection of low molecular weight cysteine proteinase inhibitors by time-resolved fluoroimmunoassay", J immunol Methods, 86(2):243-7 (1986).

Feldman et al., "Cystain B as a tissue and urinary biomarker of bladder cancer recurrence and disease progression", Clin Cancer Res, 15(3):1024-31 (2009).

Abrahamson et al., "Isolation of Six Cysteine Proteinase Inhibitors with special reference to kidney failure", Scand J Clin Lab Invest, 45:11-16 (985).

Puppione et al., "Mass spectral analysis of the apolipoproteins on dog (Canis lupus fariliaris) high density lipoproteins. Detection of apolyprotein A-II", Comparative Biochemistry and Physiology, pp. 290-296 (2008).

Assaife-Lopes et al., "Adenosine deamination to inosine in isolated basolateral membrane from kidney proximal tubule: implication for modulation of the membrane-protein kinase A", Archives of Biochemistry and Biophysics, 486:44-50 (2009).

Nishiyama et al., "Renal interstitial adenosine metabolism during ischemia in dogs", Am. J. Physiol. Renal Physiol., 280:F231-238 (2001).

Guinzberg et al., "Inosine released after hypoxia activates hepatic glucose liberation through A3 adenosine receptors", Am. J. Physiol. Endocrinol. Metab., 290:E940-951 (2006).

Modis et al., "Cytoprotective effects of adenosine and inosine in an in vitro model of acute tubular necrosis", Br. J. Pharmacol., 158:1565-1578 (2009).

Chio et al., "Dialysis modality-dependent changes in serum metabolites: accumulation of inosine and hypoxanthine in patients on haemodialysis", Nephorl. Dial. Transplant, 26:1304-1313 (2011).

Zhang et al., "Identification of novel serum biomarkers in child nephroblastoma using proteomics technology", Mol. Biol. Rep. 38:631-638 (2011).

Gursky et al., "Thermodynamic Analysis of Human Plasma Apolipoprotein C-1: High-Temperature Unfolding and Low-Temperature Oligomer Dissociation", Biochemistry, 37:1283-1291 (1998).

Dieterie et al., "Urinary clusterin, cystatin C, B2-microglobin and total protein as markers to detect drug-induced kidney injury", Nature Biotechnology, 28(5):463-469 (2010).

Bonavida et al., "Anti-Inosine Antibodies of Different Specificity Produced by Immunization with Two Immunogens", Immunochemistry, 9:445-449 (1972).

Inoye et al., "Detection of Inosine-containing Transfer Ribonucleic Acid Species by Affintiy Chromatography on Columns of Anti-Inosine Antibodies", The Journal of Biological Chemistry, 248(23):8125-8129 (1973).

Inouye et al., "Anti-Inosine Antibodies", Biochimica Et Biophysica Acta, 240:594-603 (1971).

Fatima et al., "Effect of potassium dichromate on renal brush border membrane enzymes and phosphate transport in rats", Human & Experimental Toxicology, 24:631-638 (2005).

Nabity et al., "Day-to-Day Variation of the Urine Protein: Creatinine Ratio in Female Dogs with Stable Glomerular Proteinuria Caused by X-Linked Hereditary Nephropathy", J. Vet Intern Med, 21:425-430 (2007).

Ruegg et al., "Differential Patterns of injury to the Proximal Tubule of Renal Cortical Slices following in vitro Exposure to Mercuric Chloride, Potassium Dischromate, or Hypoxic Conditions", Toxicology and Applied Pharmacology, 90:261-273 (1987).

Tenorio-Velazquez et al., "Hypothyroidism attenuates protein tyrosine nitration, oxidative stress and renal damage induced by ischemia and reperfusion: effect unrelated to antioxidant enzymes activiates", BMC Nephrology, 6:4 (2005).

Chiosolo et al., "Kidney Injury Molecule-1 Expression in Rat Proximal Tubule after Treatment with Segment-Specific Nephrotoxicants: A Tool for Early Screening of Potential Kidney Toxicity", Toxicologic Pathology, 38:338-345 (2010).

Jerala et al., "Cloning a synthetic gene for human stefin B and its expression in E. coli.", FEBS Lett. 239(1):414, Oct. 24, 1998.

Forterre et al., "Protein profiling of urine from dogs with renal disease using ProteinChip analysis", J Vet Diagn Invest, 16:271-277 (2007).

Cowgill et al., "Role of hemodialysis in the management of dogs and cats with renal failure", Vet Clin North Am Small Anim Pract, 26(6):1347-78, Nov. 1996 (Abstract Only).

Khan et al., "Expression of Cyclooxygenase-2 in Canine Renal Cell Carcinoma", et Pathol 38:116-119 (2001).

Selvarajah et al., "Gene expression profiling of canine osteosarcoma reveals genes associated with short and long survival times", Molecular Cancer, 8:72, pp. 1-18 (2009).

Anderson, "The Clinical Plasma Proteome: A Survey of Clinical Assays for Proteins in Plasma Serum," Clinical Chemistry, 56:2, 177-185 (2010).

Labome, CSTB (CystatinB, CPIB, Stefin B, CST6, STFB, Liver Thiol Proteinase Inhibitor, StefinB) | US Biological S797286F product information, retrieved from https:www.labome.com/product/US-Biological/S7972-86F.html on May 1, 2017, 2 pages.

Grauer, Staging and management of canine chronic kidney disease, retrieved from http://veterinarynews.dvm360.com/stagingandmanagementcaninechronickidneydisease?id=pageID=1&sk=&date= on Feb. 12, 2016 2 pages.

Database Geneseq [Online] Feb. 3, 2011, "Human org 32987", EBI accession No. GSP:AUN31646.

Hopsu-Havu et al., "Serum cysteine proteinase inhibitors with special reference to kidney failure", Scand J Clin Lab Invest, 45:11-16 (1985).

\* cited by examiner

MARKERS FOR RENAL DISEASE

CROSS REFERENCE TO RELATED APPLICATIONS

This application is a divisional application of U.S. application Ser. No. 13/700,992, filed on Jan. 30, 2013, which is a U.S. National Stage Application of PCT/US2011/039122, filed on Jun. 3, 2011, which claims the benefit of U.S. Provisional Application Nos. 61/351,183, filed Jun. 3, 2010, and 61/411,280 filed Nov. 8, 2010, all of which are incorporated herein by reference in their entireties.

SEQUENCE LISTING

This document incorporates by reference an electronic sequence listing text file. The text file is named 10712WOUSSL.txt, is 14.0 kilobytes, and was created on Jan. 29, 2013.

BACKGROUND OF THE INVENTION

Renal disease is associated with increased water consumption, frequent urination, diminished appetite, weight loss and muscle atrophy. Generally, by the time clinical symptoms of renal disease develop, irreparable kidney damage has occurred. Early detection permits earlier treatment and in turn slows disease progression. Current treatment includes dialysis and a diet low in phosphorous and protein. Unfortunately, no cure for chronic renal disease exists and kidney failure will eventually occur. Therefore, early detection is crucial for improved life span and quality of life.

In mammals, renal disease progression is divided into five levels. Current methods for detecting canine renal disease include kidney ultrasound, biopsy, or measurement of urine protein/creatinine levels. Biopsy is invasive and creatinine measurement is not accurate until stage three of renal failure, which is after significant tissue damage has occurred. Methods for detecting canine renal disease at earlier stages are needed in the art as such methods would inhibit disease progression.

SUMMARY OF THE INVENTION

This invention provides reagents and methods for identifying patients with renal disease. The reagents and methods of this invention are directed to detecting levels of specific metabolites, full-length proteins and protein fragments, particularly inosine nucleoside and the following proteins: apolipoprotein C-I, apolipoprotein C-II, fibrinogen alpha chain, or fibrinogen A-alpha chain, kininogen, keratin Type I cytoskeletol 10, cystatin A, cystatin B, Inter-Alpha Inhibitor H4 (ITIH4) and/or one or more of SEQ ID NOs:1-59 in renal patient samples. The relative levels of full-length protein and protein fragment provide biomarkers for diagnosing kidney/renal disease. Reagents and methods of this invention are additionally directed to assessing inosine concentrations as a biomarker for kidney/renal disease. Specific embodiments of the reagents and methods of the described invention are adapted for detecting protein biomarkers specific to renal disease. In one embodiment, antibodies specific for SEQ ID NOS: 3, 7, 13, or 20 are used to bind proteins and protein fragments produced in patients with renal disease; a non-limiting example of such proteins identified herein include apolipoprotein C-I, apolipoprotein C-II, fibrinogen alpha chain, or fibrinogen A-alpha chain. In a further embodiment, antibodies are specific for CysB1, Cys A, Kininogen, Inter-Alpha Inhibitor H4 (ITIH4), or keratin type I cytoskeletal 10. In a particular embodiment, methods for assessing the differential levels of inosine provide a biomarker for renal disease. Inosine levels may be assessed, for example, by LC/MS or inosine-specific antibodies. In additional embodiments, the reagents and methods provided herein detect altered protein levels in blood, serum, plasma, or urine. A plurality of altered protein and protein fragments are disclosed herein that occur in renal disease, including but not limited to amino acid sequences set forth in greater detail (see Table 1). Certain embodiments of the invention also provide one or a plurality of polypeptide sequences disclosed herein that exhibit altered levels in renal patient samples. In additional embodiments, the invention provides diagnostic methods using antibodies specific to one or a plurality of polypeptides consisting of SEQ ID NOS: 1-59 for identifying renal disease.

An embodiment of the invention provides antibodies that specifically bind to one or a plurality of polypeptides consisting of SEQ ID NOS: 1-59. In a preferred embodiment, the invention provides an antibody that specifically binds to a polypeptide consisting of SEQ ID NOS: 3, 7, 13, or 20. An antibody specific for the above SEQ ID NOS: binds full-length proteins, truncated proteins, or protein fragments comprising the respective SEQ ID. The invention further provides an antibody that specifically binds canine apolipoprotein C-I, apolipoprotein C-II, fibrinogen alpha chain, or fibrinogen A-alpha chain. The invention further provides an antibody that specifically binds canine CysB1, Cys A, Kininogen, Inter-Alpha Inhibitor H4 (ITIH4), or keratin type I cytoskeletal 10. The antibody can be a monoclonal antibody, polyclonal antibody, antigen-binding antibody fragment, or a single chain antibody.

Another embodiment of the invention provides a method of diagnosing renal disease in a subject. The method comprises obtaining a biological sample from the subject; contacting the biological sample with an antibody specific for one or a plurality of SEQ ID NOS: 1-59 under conditions that allow polypeptide/antibody complexes to form; and detecting the levels of polypeptide/antibody complexes relative to levels present in control samples. In a preferred embodiment, a diagnostic antibody is specific for one or a plurality of SEQ ID NOS: 3, 7, 13, or 20, wherein the antibodies respectively specifically bind apolipoprotein C-I, apolipoprotein C-II, fibrinogen alpha chain, or fibrinogen A-alpha chain. The invention further provides an antibody that specifically binds canine Cystatin B, Cystatin A, Kininogen, Inter-Alpha Inhibitor H4 (ITIH4), or keratin type I cytoskeletal 10.

Yet another embodiment of the invention provides a method of detecting renal failure by identifying one or a plurality of polypeptides specific to SEQ ID NOS: 1-59 in a sample. The method comprises contacting antibodies that specifically bind to a polypeptide consisting of SEQ ID NOS: 1-59 with the sample under conditions that allow polypeptide/antibody complexes to form; and detecting the polypeptide/antibody complexes, wherein the differential levels of polypeptide/antibody complexes formed with patient sample versus control sample is an indication of renal disease. In an alternative embodiment, the method comprises contacting antibodies that specifically bind SEQ ID NOS: 3, 7, 13, or 20, wherein the antibodies respectively specifically bind apolipoprotein C-I, apolipoprotein C-II, fibrinogen alpha chain, or fibrinogen A-alpha chain. In yet another embodiment the antibodies specifically bind full-length proteins, truncated proteins, or protein fragments containing the respective SEQ ID.

The detection of the levels of polypeptide/antibody complexes present in the sample at differential levels to those of control samples (i.e., non-diseased) is an indication renal disease. In one embodiment of the invention the levels of polypeptide/antibody complexes in a patient sample at greater levels than controls is an indication of disease. In an alternative embodiment, the levels of polypeptide/antibody complexes in a patient at levels less than control is an indication of disease, particularly for inosine-specific antibodies. The antibodies can be monoclonal antibodies, polyclonal antibodies, antigen-binding antibody fragments, or single chain antibodies. The antibodies can specifically full-length proteins, truncated proteins, or protein fragments containing the respective SEQ ID NOS. In certain embodiments the inventive methods use metabolomics (i.e., LC/MS), and the biomarkers identified thereby, provide a significant improvement over current methods of detection. Instead of analyzing a solid tissue sample, cellular products or proteins are identified in patient biofluid or serum samples. This type of testing could reduce patient discomfort, permit repeated measurement, and allow more timely assessments.

One embodiment of the invention provides for one or a plurality of purified polypeptide comprising SEQ ID NOS: 1-59, wherein the polypeptide consists of less than about 40, 30, 20, or 10 contiguous naturally occurring amino acids; SEQ ID NOS: 1-3, wherein the polypeptide consists of less than about 30 contiguous naturally occurring apolipoprotein C-I amino acids; SEQ ID NOS: 4-7, wherein the polypeptide consists of less than about 40 contiguous naturally occurring fibrinogen A-alpha chain amino acids; SEQ ID NOS: 8-13, wherein the polypeptide consists of less than about 40 contiguous naturally occurring apolipoprotein C-II amino acids; or SEQ ID NOS: 14-20, wherein the polypeptide consists of less than about 20 contiguous naturally occurring fibrinogen alpha chain amino acids; SEQ ID NOS: 21-24, wherein the polypeptide consists of less than about 20 contiguous naturally occurring Kininogen chain amino acids; SEQ ID NOS: 25-28, wherein the polypeptide consists of less than about 30 contiguous naturally occurring Inter-Alpha Inhibitor H4 (ITIH4) chain amino acids; SEQ ID NOS: 29-31, wherein the polypeptide consists of less than about 20 contiguous naturally occurring CysA chain amino acids; SEQ ID NOS: 32-38, wherein the polypeptide consists of less than about 20 contiguous naturally occurring CysB1 chain amino acids; SEQ ID NOS: 39-59, wherein the polypeptide consists of less than about 30 contiguous naturally occurring keratin Type I cytoskeletol 10 chain amino acids. The invention also provides isolated polynucleotides that encode the purified polypeptide of the invention.

Therefore, the invention provides compositions and methods for the detecting, diagnosing, or prognosing renal disease.

Specific embodiments of this invention will become evident from the following more detailed description of certain preferred embodiments and the claims.

BRIEF DESCRIPTION OF THE DRAWINGS

These and other objects and features of this invention will be better understood from the following detailed description taken in conjunction with the drawings wherein.

DETAILED DESCRIPTION OF THE PREFERRED EMBODIMENTS

Figure 1:
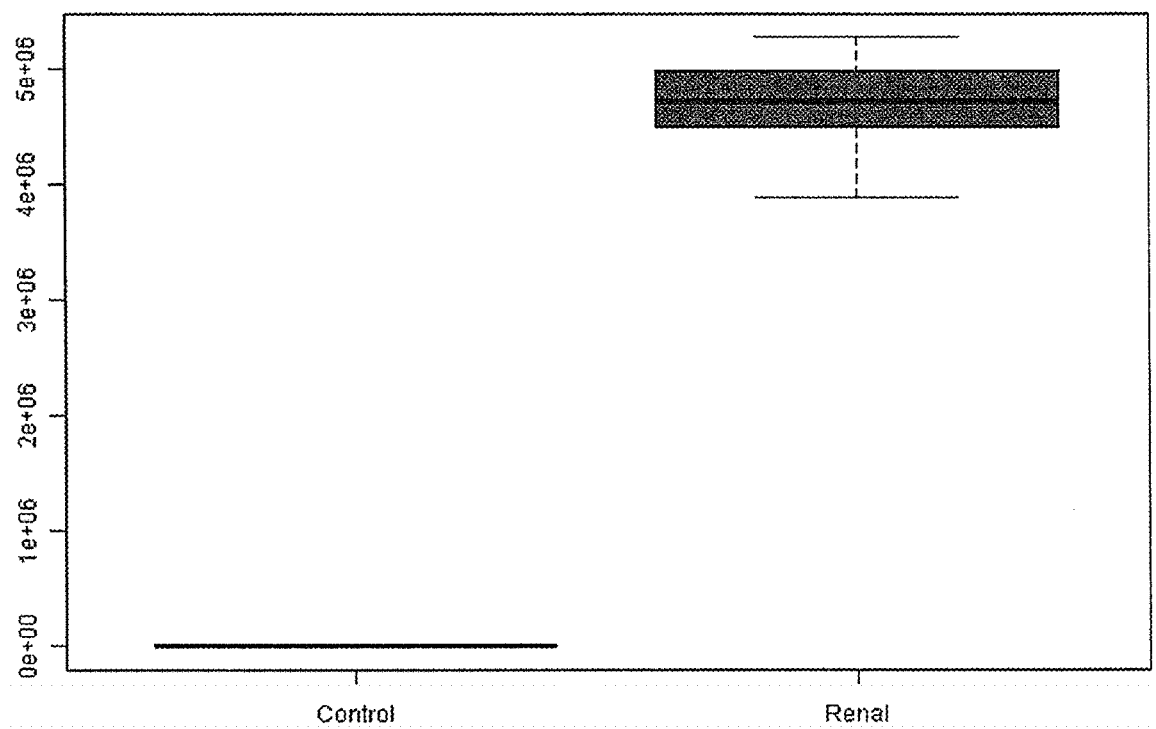
FIG. 1 is a graph representing LC/MS measurement of inosine levels between high creatinine and control (low creatinine) dogs.

This invention is more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The terms used in the specification generally have their ordinary meanings in the art, within the context of the invention, and in the specific context where each term is used. Some terms have been more specifically defined below to provide additional guidance to the practitioner regarding the description of the invention.

In other embodiments, the invention provides methods for detecting the polypeptides provided in Table 1, wherein the relative levels of the disclosed polypeptides identifies patients with renal disease. In the application and practice of these inventive methods, any method known in the art for detecting polypeptides can be used. In certain embodiments, these methods are practiced by identifying expression levels of full-length protein and polypeptide fragments of apolipoprotein C-I, apolipoprotein C-II, fibrinogen alpha chain, or fibrinogen A-alpha chain, CysB1, Cys A, Kininogen, Inter-Alpha Inhibitor H4 (ITIH4), or keratin type I cytoskeletal 10 in patient samples, wherein differential expression of the proteins as compared to a control are an indication of renal disease. In alternative embodiments, immunohistochemical (IHC) methods are used to detect renal disease in kidney biopsies.

In a particular embodiment, the invention provides methods for detecting inosine levels and other protein/metabolite levels in patient samples relative to controls. Relative levels can be measured by LC/MS (liquid chromatography/mass spectrometry). Alternatively, inosine and/or protein levels can be assessed with specific antibodies. For anti-inosine antibodies, see, Inouye, H. et al., Biochim Biophys Acta 1971, 240:594-603; Bonavida, B. et al., Immunochemistry 1972, 9:443-49; Inouye, H. et al., J Biol Chem 1973, 23:8125-29. Reduced levels of inosine are indicative of kidney/renal disease.

As used herein, a "patient" or "subject" to be treated by the disclosed methods can mean either a human or non-human animal but in certain particular embodiments is a human feline, or canine.

The term "patient sample" as used herein includes but is not limited to a blood, serum, plasma, or urine sample obtained from a patient.

The term "control sample" as used herein can mean a sample obtained from a non-diseased individual or population, more particularly an individual or population that does not suffer from renal disease.

The term "polypeptides" can refer to one or more of one type of polypeptide (a set of polypeptides). "Polypeptides" can also refer to mixtures of two or more different types of polypeptides (i.e., a mixture of polypeptides that includes but is not limited to full-length protein, truncated protein, or protein fragments). The terms "polypeptides" or "polypeptide" can each also mean "one or more polypeptides."

The term "full-length" as used herein refers to a protein comprising its natural amino acid sequence as expressed in vivo, or variants thereof. The term "truncated" refers to a protein that is lacks amino acids from the N- or C-terminal ends of the protein. The term "peptide fragment" refers to a partial amino acid sequence from a larger protein. In particular embodiments, a peptide fragment is 10, 20, 30, 40, or 50 amino acids in length.

As disclosed herein, the polypeptides identified and provided by this invention comprise one or a plurality of proteins that have altered expression (e.g., either increased or decreased) in patients with renal disease. In certain embodiments, aberrant levels of the polypeptides set forth herein are associated with renal dysfunction; in particular, increased apolipoprotein C-I, increased apolipoprotein C-II, decreased fibrinogen A-alpha chain, or decreased fibrinogen alpha chain polypeptide fragments as detected inter alia by antibodies specific to the polypeptides of the invention. In certain embodiments aberrant levels of additional polypeptides and proteins are included and in particular inosine metabolite and the following proteins: apolipoprotein C-I, apolipoprotein C-II, fibrinogen alpha chain, or fibrinogen A-alpha chain, kininogen, and Inter-Alpha Inhibitor H4 (ITIH4). In some embodiments, the proteins are found in blood, serum, plasma, or urine. The relative levels of specific polypeptides can indicate progression of renal failure and disease severity.

In either embodiment, altered protein expression is relative to control (e.g., non-renal diseased) sample comprising the invention show differential expression levels as compared to control samples. This invention provides antibodies specific to the polypeptides of Table 1 and methods of use thereof for identifying renal disease, in patient samples and to provide prognosis and diagnosis thereby. It is an advantage of this invention that altered expression of the polypeptides provided herein can be readily detected using methods well known to the skilled worker.

In particular embodiments, the invention provides reagents and methods for identifying renal disease in a mammal, and more particularly, in dogs, cats and humans. In certain embodiments, the invention provides methods for providing a diagnosis and prognosis for a renal patient. As disclosed herein, identifying the polypeptides of this invention in patient samples can be an independent predictor of kidney disease or an identifier of disease stage (e.g., stages 1-5). This invention advantageously permits diagnosis and identification of kidney disease stage prior to stage three and is not limited by patient age or body mass. Accordingly, additional embodiments of the invention are directed to using said renal patient prognosis determined using the polypeptides of the invention to select appropriate renal therapies.

For the purposes of this invention, the term "immunological reagents" is intended to encompass antisera and antibodies, particularly monoclonal antibodies, as well as fragments thereof (including F(ab), F(ab)$_2$, F(ab)' and F$_v$ fragments). Also included in the definition of immunological reagent are chimeric antibodies, humanized antibodies, and recombinantly-produced antibodies and fragments thereof. Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), radioimmune assay (RIA), as well as peroxidase labeled secondary antibodies that detect the primary antibody.

The immunological reagents of the invention are preferably detectably-labeled, most preferably using fluorescent labels that have excitation and emission wavelengths adapted for detection using commercially-available instruments such as and most preferably fluorescence activated cell sorters. Examples of fluorescent labels useful in the practice of the invention include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to immunological reagents, such as antibodies and most preferably monoclonal antibodies using standard techniques (Maino et al., 1995, *Cytometry* 20: 127-133).

Antibodies of the invention are antibody molecules that specifically bind to polypeptides of the invention as provided in Table 1, variant polypeptides of the invention, or fragments thereof. An antibody of the invention can be specific for polypeptide fragments of apolipoprotein C-I, apolipoprotein C-II, fibrinogen alpha chain, or fibrinogen A-alpha chain, for example, an antibody specific for one or a plurality of SEQ ID NOS: 3, 7, 13, or 20. An antibody of the invention preferably recognizes multiple protein products. For example an antibody specific to SEQ ID NO: 3 recognizes multiple peptide fragment of apolipoprotein C-I, including SEQ ID NOS: 1-2, as well as full-length protein. One of skill in the art can easily determine if an antibody is specific for a polypeptide of Table 1 using assays described herein. An antibody of the invention can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antigen binding antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds," "specifically bind," or "specific for" means that a first antigen, e.g., a polypeptide of Table 1, recognizes and binds to an antibody of the invention with greater affinity than to other, non-specific molecules. "Specifically binds," "specifically bind" or "specific for" also means a first antibody, e.g., an antibody raised against SEQ ID NOS:1-59, recognizes and binds to SEQ ID NOS:1-59, with greater affinity than to other non-specific molecules. A non-specific molecule is an antigen that shares no common epitope with the first antigen. Specific binding can be tested using, for example, an enzyme-linked immunosorbant assay (ELISA), a radioimmunoassay (RIA), or a western blot assay using methodology well known in the art.

The phrase "competes for binding" as used herein refers to an antibody that has a binding affinity for a particular polypeptide sequence or antigen such that when present, it will bind preferentially and specifically to the peptide sequence/antigen over other non-specific molecules. Again, a non-specific molecule is an antigen that shares no common epitope with the first antigen.

Antibodies of the invention include antibodies and antigen binding fragments thereof that (a) compete with a reference antibody for binding to SEQ ID NOS: 1-59 or antigen binding fragments thereof; (b) binds to the same epitope of SEQ ID NOS: 1-59 or antigen binding fragments thereof as a reference antibody; (c) binds to SEQ ID NOS: 1-59 or antigen binding fragments thereof with substantially the same $K_d$ as a reference antibody; and/or (d) binds to SEQ ID NOS: 1-59 or fragments thereof with substantially the same off rate as a reference antibody, wherein the reference antibody is an antibody or antigen-binding fragment thereof that specifically binds to a polypeptide of SEQ ID NOS: 1-59 or antigen binding fragments thereof with a binding affinity $K_a$ of $10^7$ l/mol or more.

The affinity of a molecule X for its partner Y can be represented by a dissociation constant (Kd). The equilibrium dissocation constant (Kd) is calculated at the ration of $k_{off}/k_{on}$. See Chen, Y. et al., 1999, J. Mol. Biol. 293: 865-881. A variety of methods are known in the art for measuring affinity constants, which can be used for purposes of the present invention. In a particular embodiment, the reference antibody is an antibody or antigen-binding fragment thereof that has a binding affinity to a polypeptide of SEQ ID NOS: 1-59 with a particular $K_{on}$ rate/association rate or $K_{off}$ rate. In one embodiment, the antibodies of the invention specifically bind with a $K_{on}$ of $6\times10^5$ $M^{-1}s^{-1}$ or better; antibodies specifically bind with a $K_{off}$ rate of $5\times10^{-6}$ $s^{-1}$ or better; or antibodies specifically binds with a binding affinity of 500 pM, 400 pM, 300 pM, 200 pM, 100 pM, 50 pM, 40 pM, 30 pM, 20 pM or better.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing polypeptide-specific antibodies can be identified using RIA or ELISA and isolated by cloning in semi-solid agar or by limiting dilution. Clones producing specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. Nos. 4,474,893; 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), caninized, canine, or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind SEQ ID NOS: 1-59 are particularly useful for detecting the presence of polypeptide fragments specific for renal disease present in a sample, such as a serum, blood, plasma, cell, tissue, or urine sample from an animal. An immunoassay for can utilize one antibody or several antibodies. An immunoassay can use, for example, a monoclonal antibody specific for one epitope, a combination of monoclonal antibodies specific for epitopes of one polypeptide, monoclonal antibodies specific for epitopes of different polypeptides, polyclonal antibodies specific for the same antigen, polyclonal antibodies specific for different antigens, or a combination of monoclonal and polyclonal antibodies Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or antigen-binding fragments thereof can be bound to a support and used to detect the presence of proteins differential produced in renal disease. Supports include, for example, glass, polystyrene, polypropylene, polyethylene, dextran, nylon, amylases, natural and modified celluloses, polyacrylamides, agaroses and magletite.

Antibodies of the invention can further be used to isolate polypeptides by immunoaffinity columns. The antibodies can be affixed to a solid support by, for example, absorption or by covalent linkage so that the antibodies retain their immunoselective activity. Optionally, spacer groups can be included so that the antigen binding site of the antibody remains accessible. The immobilized antibodies can then be used to bind the polypeptides of Table 1 from a biological sample, including but not limited to saliva, serum, blood, and urine.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a kidney disease. By measuring the increase or decrease of antibodies specific for the polypeptides of Table 1 in a test sample from an animal, it can be determined whether a particular therapeutic regiment aimed at ameliorating the disorder is effective. Antibodies can be detected and/or quantified using for example, direct binding assays such as RIA, ELISA, or Western blot assays.

The methods of the invention can be used to detect polypeptide fragments of Table 1 or full-length proteins containing an amino acid sequence provided in Table 1, wherein antibodies or antigen-binding antibody fragments are specific for SEQ ID NOS: 1-59. A biological sample can include, for example, sera, blood, cells, plasma, saliva, or urine from a mammal such as a dog, cat or human. The test sample can be untreated, precipitated, fractionated, separated, diluted, concentrated, or purified.

In one embodiment methods of the invention comprise contacting a test sample with one or a plurality of antibodies specific to SEQ ID NOS: 1-59 under conditions that allow polypeptide/antibody complexes, i.e., immunocomplexes, to form. That is, antibodies of the invention specifically bind to one or a plurality of polypetides of SEQ ID NOS: 1-59 located in the sample. One of skill in the art is familiar with assays and conditions that are used to detect antibody/polypeptide complex binding. The formation of a complex between polypeptides and antibodies in the sample is detected. The formation of antibody/polypeptide complexes is an indication that polypeptides are present in the patient sample.

Antibodies of the invention can be used in a method of the diagnosis renal disease by obtaining a test sample from, e.g., a human, cat or dog suspected of suffering from renal disease. The test sample is contacted with antibodies of the invention under conditions enabling the formation of antibody-antigen complexes (i.e., immunocomplexes). One of skill in the art is aware of conditions that enable and are appropriate for formation of antigen/antibody complexes. The amount of antibody-antigen complexes can be determined by methodology known in the art.

Methods of the invention comprise diagnosing renal disease in a patient by identifying the differential expression of the polypeptides of Table 1 in a patient sample as compared to control. These methods include the diagnosis or identification of disease stage (e.g., stages 1-5). The present invention further include methods for prognosing patient health, monitoring disease progression, and/or assessing/monitoring treatment efficacy by identifying levels of specific polypeptides of the invention in a patient sample. In one aspect, the inventive methods can be performed at multiple time points to evaluate disease progression or treatment efficacy. In a particular embodiment, the methods may be performed at diagnosis and then at specific time points post-treatment wherein a specific therapy should result in a reduction or amelioration of disease progression.

In an alternative embodiment, the methods of the invention are used to assess the efficacy of a composition or treatment regime (whether a composition or diet) for the amelioration of renal disease progression. Similarly, the methods of the invention can be used for assessing a composition or treatment regimens activity on patient levels of the polypeptides of Table 1.

Differential levels of antibody-complexes present in patient samples versus control samples provides an indicator for renal disease. In one embodiment of the invention an antibody is specific for one or plurality of the polypeptides provided in Table 1. An antibody of the invention can be contacted with a test sample. Antibodies specific to the polypeptides present in a test sample will form antigen-antibody complexes under suitable conditions. The amount of antibody-antigen complexes can be determined by methods known in the art.

In one embodiment of the invention, renal disease can be detected in a subject. A biological sample is obtained from the subject. One or more antibodies specific to the polypeptides comprising SEQ ID NOS:1-59 or other polypeptides of the invention are contacted with the biological sample under conditions that allow polypeptide/antibody complexes to form. The polypeptide/antibody complexes are detected. The detection of the polypeptide/antibody complexes at differential levels as compared to controls is an indication that the mammal has renal disease.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, one or more antibodies of the invention are attached to a solid phase or substrate. A test sample potentially comprising a protein comprising a polypeptide of the invention is added to the substrate. One or more antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, one or more antibodies of the invention are attached to a solid phase or substrate. A test sample potentially containing a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise and indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

In one embodiment, one or more capture antibodies can specifically bind to one or more epitopes of a polypeptide of the invention. The capture antibody or antibodies would be used to immobilize one or a plurality of polypeptide of SEQ ID NOS: 1-59 to, for example a solid support. One or more detection antibodies can specifically bind to the same one or more epitopes or different one or more epitopes of the polypeptides of the invention. The detection antibody can be used to detect or visualize the immobilization of the polypeptide of the invention to a solid support. This embodiment is advantageous because it is more specific and more sensitive than assays using only one antibody for both capture and detection functions.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See e.g., U.S. Pat. No. 5,726,010.

Assays can use solid phases or substrates or can be performed by immunoprecipitation or any other methods that do not utilize solid phases. Where a solid phase or substrate is used, one or more polypeptides of the invention are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment of the invention a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing antibodies on solid phases include ionic, hydrophobic, covalent interactions and the like.

In one type of assay format, one or more antibodies can be coated on a solid phase or substrate. A test sample suspected of containing polypeptides of Table 1 or fragments thereof is incubated with an indicator reagent comprising a signal generating compound conjugated to an antibodies or antibody fragments specific for said polypeptides for a time and under conditions sufficient to form antigen/antibody complexes of either antibodies of the solid phase to the test sample polypeptides or the indicator reagent compound conjugated to an antibody specific for the polypeptides. The binding of the indicator reagent conjugated to anti-polypeptide antibodies to the solid phase can be quantitatively measured. A measurable alteration in the signal compared to the signal generated from a control sample indicates the presence of polypeptides of the present invention (SEQ ID NOS: 1-59). This type of assay can quantitate the amount of polypeptide in a test sample.

In another type of assay format, one or more antibodies of the invention are coated onto a support or substrate. An antibody of the invention is conjugated to an indicator reagent and added to a test sample. This mixture is applied to the support or substrate. If polypeptides of the invention are present in the test sample, they will bind the one or more antibodies conjugated to an indicator reagent and to the one or more antibodies immobilized on the support. The polypeptide/antibody/indicator complex can then be detected. This type of assay can quantitate the amount of polypeptide in a test sample.

In another type of assay format, one or more antibodies of the invention are coated onto a support or substrate. The test sample is applied to the support or substrate and incubated. Unbound components from the sample are washed away by washing the solid support with a wash solution. If the polypeptides of Table 1 are present in the test sample, they will bind to the antibody coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of polypeptides in a test sample.

The formation of a polypeptide/antibody complex or a polypeptide/antibody/indicator complex can be detected by, for example, radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex at differential levels as compared to control is indicative of the presence of renal disease. Therefore, the methods of the invention can be used to diagnose kidney disease in an animal.

The phrase "determining the amounts" as used herein refers to measuring or identifying the levels of one or a plurality polypeptides in a patient sample. In a particular embodiment, the identification of a specific epitope in polypeptides of multiple lengths including full-length protein, truncated protein, and protein fragments is provided. This can be accomplished by methodology well known in the art for the detection of polypeptides including using antibodies including, for example enzyme-linked immunosorbant assay (ELISA), a radioimmunoassay (RIA), or a western blot assay, or immunohistochemistry. Alternatively polypeptides of the present invention, SEQ ID NOS: 1-59, can be determined by mass spectrometry or similar methods known by one of skill in the art. Determining the amount of polypeptide present in a patient sample is accomplished by such in vitro analysis and experimental manipulation. The amount of polypeptide present cannot be assessed by mere inspection.

In an alternative embodiment, elevated or reduced levels of one or a plurality of polypeptide transcripts of Table 1 present in a patient sample are detected by a process of hybridizing a nucleic acid probe that selectively hybridizes to the polypeptides of the invention. Conditions are utilized that permit high stringency hybridization between the nucleic acid probe, which is used as a detection means, and the polypeptide transcripts of the invention, wherein a level of nucleic acid complex formation and detection is indicative of the level of transcript in a sample. The enhanced or reduced level of polypeptide is indicative of renal disease. Methods for producing nucleic acid probes specific to the polypeptide transcripts are well known in the art.

The methods of the invention can also indicate the amount or quantity of polypeptides of Table 1 or full-length proteins comprising a polypeptide sequence of Table 1 in a test sample. In a particular embodiment, the amount or quantity of certain polypeptides provides an indicator of disease stage (i.e., stages 1-5), disease progression, and/or a prognostic indicator. With many indicator reagents, such as enzyme conjugates, the amount of polypeptide present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrated specimens such as urine, in order to determine the presence and/or amount of polypeptide present.

Polypeptides and assays of the invention can be combined with other polypeptides or assays to detect the presence of renal disease. For example, polypeptides and assays of the invention can be combined with reagents that creatinine or general protein levels.

The invention also provides kits for performing the methods disclosed herein. In certain embodiments, the kits of this invention comprise one or a plurality of antibodies specific for one or plurality of the polypeptides provided in Table 1, wherein in particular embodiments said antibody are monoclonal antibodies, polyclonal antibodies, antigen-binding antibody fragments, or single chain antibodies. Optionally included in specific embodiments of the kits of the invention can be instructions for use, as well as secondary antibodies useful inter alia in sandwich assays understood by those in the art. Distinguishingly labeled embodiments of the antibody components of said kits, as well as reagents and methods for labeling said antibodies, are also advantageously-provided components of the kits of the invention.

In further embodiments, kits of the invention comprise one or plurality of antibodies that each specifically bind to differential protein expression of one or a plurality of the polypeptides identified in Table 1. In certain embodiments, said antibodies are provided on a solid support, including without limitation chips, microarrays, beads and the like. Optionally included in specific embodiments of the kits of the invention can be instructions for use, as well as secondary antibodies useful inter alia in sandwich assays understood by those in the art. Distinguishingly labeled embodiments of the antibody components of said kits, as well as reagents and methods for labeling said antibodies, are also advantageously-provided components of the kits of the invention.

The kits of the present invention (e.g., articles of manufacture) are for detecting the polypeptides of Table 1, or protein fragment thereof in a patient sample. A kit comprises one or more antibodies of the invention and means for determining binding of the antibodies to full-length proteins or protein fragments containing the amino acid sequences provided in Table 1 present in the sample. A kit or article of manufacture can also comprise one or more antibodies or antibody fragments of the invention and means for determining binding of the antibodies or antibody fragments to polypeptides in the sample. A kit can comprise a device containing one or more polypeptides or antibodies of the invention and instructions for use of the one or more polypeptides or antibodies for, e.g., the identification of renal disease in a mammal. The kit can also comprise packaging material comprising a label that indicates that the one or more polypeptides or antibodies of the kit can be used for the identification of kidney dysfunction. Other components such as buffers, controls, and the like, known to those of ordinary skill in art, can be included in such test kits. The polypeptides, antibodies, assays, and kits of the invention are useful, for example, in the diagnosis of individual cases of renal disease in a patient.

The kits of the invention are useful for diagnosing, prognosing, or monitoring the treatment of renal disease, particularly canine renal disease.

One embodiment provides a purified polypeptide comprising SEQ ID NOS:1-59, wherein the polypeptide consists of less than about 50, 40, 35, 30, 25, 20, 15, 10 (or any range between about 31 and about 175) contiguous naturally occurring amino acids. In one embodiment of the invention a purified polypeptide consists of more than about 10, 15, 20, 25, 30, 35, 40, 50, 60, contiguous naturally occurring amino acids.

The fact that polypeptides SEQ ID NOS:1-59 are smaller than the full length proteins is important because smaller polypeptides can have greater specificity and/or sensitivity than full length polypeptides assays. These smaller polypeptides can be less expensive to manufacture, and may be obtained at greater purity than the full length polypeptide. Additionally, the smaller fragments and the levels of smaller fragments present in a sample are indicative of disease state. The differential expression of fragmented proteins is a marker for renal disease.

Variant polypeptides are at least about 80%, or about 81, 82, 83, 84, 85, 86, 87, 88, 89, 90, 91, 92, 93, 94, 95, 96, 97, 98, or 99% identical to the polypeptide sequences shown in SEQ ID NOS:1-59 and are also polypeptides of the invention. For example, a variant polypeptide of SEQ ID NOS: 1-59 can be about at least 97%, 94%, 90%, 87%, 84%, or 81% identical to SEQ ID NOS:1-59. Variant polypeptides have one or more conservative amino acid variations or other minor modifications and retain biological activity, i.e., are biologically functional equivalents. A biologically active equivalent has substantially equivalent function when compared to the corresponding wild-type polypeptide. In one embodiment of the invention a polypeptide has about 1, 2, 3, 4, 5, 10, 20 or less conservative amino acid substitutions.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variant polypeptides can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a different organism, a synthetic sequence, or a sequence not usually located at the carboxy or amino terminus of a polypeptide of the invention. Additionally, a polypeptide can be covalently or non-covalently linked to compounds or molecules other than amino acids, such as indicator reagents. A polypeptide can be covalently or non-covalently linked to an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more C amino acid residues at, for example, the amino terminus or carboxy terminus or both termini of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a polypeptide of the invention can be part of a fusion protein, which contains other amino acid sequences, such as amino acid linkers, amino acid spacers, signal sequences, TMR stop transfer sequences, transmembrane domains, as well as ligands useful in protein purification, such as glutathione-S-transferase, histidine tag, and *Staphylococcal* protein A. More than one polypeptide of the invention can be present in a fusion protein of the invention. A polypeptide of the invention can be operably linked to proteins of a different organism or to form fusion proteins. A fusion protein of the invention can comprise one or more of polypeptides of the invention, fragments thereof, or combinations thereof. A fusion protein does not occur in nature. The term "operably linked" means that the polypeptide of the invention and the other polypeptides are fused in-frame to each other either to the N-terminus or C-terminus of the polypeptide of the invention.

Polypeptides of the invention can be in a multimeric form. That is, a polypeptide can comprise one or more copies of a polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for the polypeptides of SEQ ID NOS: 1-59. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 30-mer polypeptide fragments (or smaller fragments), each fragment can be tested for the presence of epitopes recognized in an ELISA. For example, in an ELISA assay, a polypeptide of the invention, such as a 30-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 30-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from patient samples or cells.

An immunogenic polypeptide of the invention can comprise an amino acid sequence shown in SEQ ID NOS:1-59 or fragments thereof. An immunogenic polypeptide can elicit antibodies or other immune responses (e.g., T-cell responses of the immune system) that recognize epitopes of a polypeptide having SEQ ID NOS:1-59. An immunogenic polypeptide of the invention can also be a fragment of a polypeptide that has an amino acid sequence shown in SEQ ID NOS:1-6. An immunogenic polypeptide fragment of the invention can be about 10, 15, 20, 25, 30, 40, 50 or more amino acids in length. An immunogenic polypeptide fragment of the invention can be about 50, 40, 30, 20, 15, 10 or less amino acids in length.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Embodiments of the methods of this invention comprising the above-mentioned features are intended to fall within the scope of this invention.

EXAMPLES

The Examples that follow are illustrative of specific embodiments of the invention, and various uses thereof. They set forth for explanatory purposes only, and are not to be taken as limiting the invention.

Example 1

Identification and Purification of Blood Samples

Patient blood samples were collected from dogs. The dogs were members of a single family maintained at Texas A & M University since 1997. More specifically, this family is a colony of heterozygous (carrier) females with X-linked hereditary nephropathy (XLHN). XLHN is caused by a mutation in the gene COL4A5 which in the female dogs causes a mosaic expression of type IV collagen peptides and onset of glomerular proteinuria between 3 and 6 months of age. Nabity et al., J Vet Intern Med 2007; 21:425-430. Control versus experimental (diseased) was selected wherein controls were healthy dogs and the experimental or diseased group were dogs exhibiting elevated creatinine levels.

The following procedure was utilized for the preparation of patient samples for experimental analysis. Utilizing a 0.5 mL protein LoBind eppendorf tube, 110 uL of serum was precipitated by addition of 200 uL N,N-dimethylacetamide, which was followed by vortexing for 10 seconds, and incubating the sample at room temperature for 30 minutes. Resulting precipitate was pelleted by centrifugation at 13000 rpm for 30 minutes at 10° C. Supernatant was decanted into a borosilicate culture tube containing 5.0 mL of 0.1% formic acid in water and mixed to homogeneity.

The diluted extract was then further fractionated using a Caliper Life Science Rapid trace automated solid phase extraction apparatus as follows: 1 mL (30 mg) Waters OASIS® HLB solid phase extraction cartridges were conditioned at 0.5 mL/sec first with 1.0 mL 0.1% formic acid in water followed by 1.0 mL 0.1% formic acid in acetonitrile and finally with 2.0 mL 0.1% formic acid in water. Samples were loaded at a flow rate of 0.015 mL/sec then washed with 1.25 mL of 0.1% formic acid in water at a flow rate of 0.015 mL/sec. 1.25 mL fractions were then collected into borosilicate glass tubes containing 5 μL of 20 mg/mL N-nonyl-β-glucopyranoside in water. Fractions were eluted consecutively and collected separately using first 0.1% formic acid in 35% acetonitrile/water and next 0.1% formic acid in 65% acetonitrile/water at a flow rate of 0.015 mL/sec. The canula and solvent transfer lines were purged and cleaned between runs with 3.0 mL of 0.1% formic acid in acetonitrile then 3.0 mL of 0.1% formic acid in water at a flow rate of 0.5 mL/sec.

Fractions were split in half and evaporated to dried state at room temperature using a Savant Speed Vac Concentrator Model SVC-100H. The dried samples were then separated into two batches and stored at –80° C. For analysis, the samples were reconstituted in 60 μL 0.1% formic acid in either 5% (35% fraction) or 35% (65% fraction) acetonitrile and analyzed by liquid chromatography/mass spectrometry (LC/MS).

Example 2

Identification of Polypeptides in Diseased Dogs by Liquid Chromatography/Mass Spectrometry Experimental and control samples were subjected to liquid chromatography/mass spectrometry (LC/MS) for the identification of differentially produced polypeptides by mass. The identified polypeptide masses were then annotated to determine the corresponding protein name by performing a peptide ID search of existing databases. A unique databases for peptide annotation was created from NCBI, Swissprot, Uniprot.

The resulting data provided the polypeptides provided in Table 1. SEQ ID NOS: 1-59 are the polypeptides that were differentially produced in dogs with renal disease. Therefore, these polypeptides provide unique biomarkers for the detection renal disease in dogs.

TABLE 1

Polypeptides differentially produced in dogs with renal disease.

| Accession | No. Peptides | No. AAs | MW [kDa] | Description | Expression Levels |
|---|---|---|---|---|---|
| P56595 | 3 | 88 | 9.7 | Apolipoprotein C-I OS = Canis familiaris GN = APOC1 PE = 2 SV = 1- [APOC1_CANFA] | Increased |

TABLE 1-continued

Polypeptides differentially produced in dogs with renal disease.

| | Sequence | m/z [Da] | MH+ [Da] | RT [min] | | |
|---|---|---|---|---|---|---|
| | AGEISSTFERIPDKL KEFGNTLEDKA (SEQ. ID NO: 1) | 965.83238 | 2895.48259 | 27.98 | | |
| | EISSTFERIPDKLKE FGNTLEDKA (SEQ. ID NO: 2) | 923.14789 | 2767.42910 | 27.41 | | |
| | DKLKEFGNTLEDKA (SEQ. ID NO: 3) | 536.61725 | 1607.83719 | 20.36 | | |
| Q28243 | 4 | 443 | 45.9 | Fibrinogen A-alpha-chain (Fragment) OS = Canis familiaris PE = 4 SV = 1- [Q28243_CANFA] | | Decreased |

| | Sequence | m/z [Da] | MH+ [Da] | RT [min] | | |
|---|---|---|---|---|---|---|
| | IMGSDSDIFTNIGTP EFPSSGKTSSHSKQF VTSSTT (SEQ. ID NO: 4) | 945.45618 | 3778.80288 | 26.50 | | |
| | THIMGSDSDIFTNIG TPEFPSSGKTSSH (SEQ. ID NO: 5) | 738.34826 | 2950.37119 | 26.38 | | |
| | THIMGSDSDIFTNIG TPEFPSSGKTSSHS (SEQ. ID NO: 6) | 1013.13733 | 3037.39743 | 26.25 | | |
| | IMGSDSDIFTNIGTP EFPSSGKTSSHS (SEQ. ID NO: 7) | 933.76956 | 2799.29412 | 27.29 | | |
| P12278 | 6 | 101 | 11.2 | Apolipoprotein C-II OS = Canis familiaris GN = APOC2 PE = 2 SV = 1- [APOC2_CANFA] | | Increased |

| | Sequence | m/z [Da] | MH+ [Da] | RT [min] | | |
|---|---|---|---|---|---|---|
| | AHESQQDETTSSALL TQMQESLYSWGTARS AAEDL (SEQ. ID NO: 8) | 1335.61365 | 4004.82639 | 35.25 | | |
| | AHESQQDETTSSALL TQMQESL (SEQ. ID NO: 9) | 1217.55859 | 2434.10991 | 28.22 | | |
| | AHESQQDETTSSALL TQMQESLYSWGTA (SEQ. ID NO: 10) | 1088.15869 | 3262.46152 | 33.89 | | |
| | AHESQQDETTSSALL TQMQESL (SEQ. ID NO: 11) | 812.04224 | 2434.11216 | 28.24 | | |
| | AHESQQDETTSSALL TQMQESLYSWGTA (SEQ. ID NO: 12) | 1631.73376 | 3262.46025 | 33.91 | | |
| | AHESQQDETTSSALL (SEQ. ID NO: 13) | 808.87756 | 1616.74785 | 20.77 | | |
| P68213 | 7 | 28 | 3.0 | Fibrinogen alpha chain (Fragment) OS = Canis familiaris GN = FGA PE = 1 | | Decreased |

TABLE 1-continued

Polypeptides differentially produced in dogs with renal disease.

|  |  |  | SV = 1-[FIBA_CANFA] |  |  |  |
|---|---|---|---|---|---|---|
|  | Sequence | m/z [Da] | MH+ [Da] | RT [min] |  |  |
|  | NSKEGEFIAEGGGV (SEQ. ID NO: 14) | 697.33575 | 1393.66423 | 21.26 |  |  |
|  | SKEGEFIAEGGGV (SEQ. ID NO: 15) | 640.31421 | 1279.62114 | 21.32 |  |  |
|  | TNSKEGEFIAEGGGV (SEQ. ID NO: 16) | 747.85939 | 1494.71151 | 21.25 |  |  |
|  | KEGEFIAEGGGV (SEQ. ID NO: 17) | 596.79858 | 1192.58989 | 21.20 |  |  |
|  | EGEFIAEGGGV (SEQ. ID NO: 18) | 1064.49362 | 1064.49362 | 22.99 |  |  |
|  | GEFIAEGGGV (SEQ. ID NO: 19) | 935.44861 | 935.44861 | 22.73 |  |  |
|  | FIAEGGGV (SEQ. ID NO: 20) | 749.38739 | 749.38739 | 20.88 |  |  |
| XP_535836 | 4 | 653 | 73.1 | Kininogen |  | Decreased |
|  | Sequence | Charge | m/z [Da] | MH+ [Da] | RT [min] |  |
|  | HGGQRELDFDLEHQ (SEQ. ID NO: 21) | 3 | 560.93286 | 1680.78403 | 20.94 |  |
|  | DEEWDSGKEQGPTHGHG (SEQ. ID NO: 22) | 3 | 622.59778 | 1865.77878 | 15.61 |  |
|  | ELDFDLEHQ (SEQ. ID NO: 23) | 2 | 573.26135 | 1145.51543 | 24.10 |  |
|  | DCDYKESTQAATGEC (SEQ. ID NO: 24) | 3 | 540.87445 | 1620.60880 | 26.40 |  |
| XP_848765 & XP_843672 | 4 | 958 | 105.0 | Inter-Alpha Inhibitor H4 (ITIH4) |  | Differentially expressed |
|  | Sequence | Charge | m/z [Da] | MH+ [Da] | RT [min] |  |
|  | GSEIVVVGKLRDQSPDVLSAKV (SEQ. ID NO: 25) | 3 | 766.10455 | 2296.29911 | 24.87 |  |
|  | PRDWKPLLVPASPENVD (SEQ. ID NO: 26) | 3 | 645.01086 | 1933.01804 | 18.72 |  |
|  | ETLFSMMPGLNMTMDKTGLLL (SEQ. ID NO: 27) | 2 | 1172.08431 | 2343.16135 | 34.46 |  |
|  | AETVQ (SEQ. ID NO: 28) | 1 | 547.27649 | 547.27649 | 20.09 |  |
| XP_545130 | 66.23 | 3 | 77 | 8.8 | CysA | Differentially expressed |
|  | Sequence | Charge | m/z [Da] | MH+ [Da] | RT [min] |  |
|  | VGDNSYTHLKIFKGLP (SEQ. ID NO: 29) | 3 | 601.00467 | 1800.99945 | 26.31 |  |
|  | LTLTGYQTDKSKDDELTG (SEQ. ID NO: 30) | 3 | 662.33471 | 1984.98957 | 18.10 |  |

TABLE 1-continued

Polypeptides differentially produced in dogs with renal disease.

| | | | | | | |
|---|---|---|---|---|---|---|
| | KPQLEEKTNETYQEFEA (SEQ. ID NO: 31) | 3 | 695.32800 | 2083.96946 | 19.15 | |
| XP_535601 | 75.32 | 7 | 77 | 9.0 | CysB | Decreased |
| | Sequence | Charge | m/z [Da] | MH+ [Da] | RT [min] | |
| | YQTNKAKHDELAYF (SEQ. ID NO: 32) | 3 | 576.61572 | 1727.83261 | 21.46 | |
| | QTNKAKHDELAYF (SEQ. ID NO: 33) | 3 | 522.26111 | 1564.76877 | 20.82 | |
| | ENKPLALSSYQTNK (SEQ. ID NO: 34) | 2 | 796.91620 | 1592.82513 | 27.77 | |
| | QVVAGTPY (SEQ. ID NO: 35) | 1 | 834.43532 | 834.43532 | 31.89 | |
| | EERENKKYTTFK (SEQ. ID NO: 36) | 2 | 786.90753 | 1572.80779 | 31.24 | |
| | YFIKVQVDDDEFVHLR (SEQ. ID NO: 37) | 3 | 675.00958 | 2023.01419 | 23.40 | |
| | VVAGTPYFIKVQVDDD (SEQ. ID NO: 38) | 3 | 589.30709 | 1765.90671 | 19.41 | |
| NP_001013443 | 43.66 | 21 | 568 | 57.6 | Keratin Type I Cytoskeletal 10 | Differentially expressed |
| | Sequence | Charge | m/z [Da] | MH+ [Da] | RT [min] | |
| | MQNLNDRLAS (SEQ. ID NO: 39) | 2 | 581.28491 | 1161.56255 | 20.90 | |
| | FGGGYGGVSFGGGSFGGGSFGG (SEQ. ID NO: 40) | 3 | 624.60724 | 1871.80716 | 19.91 | |
| | SFGGGYGGVSFG (SEQ. ID NO: 41) | 2 | 546.24731 | 1091.48735 | 25.33 | |
| | FSRGSSGGGCFGGSSGGYGGLGG (SEQ. ID NO: 42) | 3 | 656.61829 | 1967.84031 | 28.01 | |
| | EEQLQ (SEQ. ID NO: 43) | 1 | 646.30862 | 646.30862 | 15.60 | |
| | QNRKDAEAWFNEKSK (SEQ. ID NO: 44) | 3 | 617.64661 | 1850.92527 | 19.80 | |
| | PRDYSKYYQTIEDLKNQI (SEQ. ID NO: 45) | 3 | 758.71680 | 2274.13584 | 26.49 | |
| | KDAEAWFNEKSKEL (SEQ. ID NO: 46) | 3 | 565.61548 | 1694.83188 | 19.42 | |
| | KYENEVALRQSVEA (SEQ. ID NO: 47) | 3 | 545.94529 | 1635.82131 | 19.39 | |
| | KSKELTTEINSNIEQM (SEQ. ID NO: 48) | 3 | 622.31818 | 1864.93998 | 19.60 | |
| | LQIDN (SEQ. ID NO: 49) | 1 | 602.31784 | 602.31784 | 16.07 | |
| | SIGGGFSSGG (SEQ. ID NO: 50) | 1 | 825.37653 | 825.37653 | 34.30 | |

TABLE 1-continued

Polypeptides differentially produced in dogs with renal disease.

| Sequence | | | |
|---|---|---|---|
| FGGGGFSGGSFGGYGGGYGGDGGLL (SEQ. ID NO: 51) | 3 | 719.64934 | 2156.93346 | 23.14 |
| LENEIQTYRSLLEGEG (SEQ. ID NO: 52) | 3 | 617.64661 | 1850.92527 | 19.80 |
| GSIGGGFSSG (SEQ. ID NO: 53) | 1 | 825.37653 | 825.37653 | 34.30 |
| EDLKNQILNLTTDN (SEQ. ID NO: 54) | 2 | 815.92169 | 1630.83611 | 26.45 |
| GGGGYGGGSSGGGGSHGGSSGG (SEQ. ID NO: 55) | 3 | 537.21368 | 1609.62650 | 19.61 |
| GRYCVQLSQIQAQISS (SEQ. ID NO: 56) | 2 | 890.94928 | 1780.89128 | 20.25 |
| RVLDELTLT (SEQ. ID NO: 57) | 1 | 1059.60266 | 1059.60266 | 33.79 |
| RLASYLDKVRALEESNY (SEQ. ID NO: 58) | 2 | 1014.02356 | 2027.03984 | 37.86 |
| GGGYGGDGGLLSGNEKV (SEQ. ID NO: 59) | 2 | 768.86627 | 1536.72527 | 22.51 |

Although methods for performing LC/MS are well known in the art, the specific liquid chromatography/mass spectrometry methods utilized for the present study are provided below:

Liquid Chromatography Parameters

Solvent A: 0.1% Formic acid in water; Solvent B: 0.1% Formic acid in acetonitrile; Column: Acquity UPLC BEH130 C18 1.7 μM 2.1 id×150 mm length; Guard Column: vanguard BEH 300 $C_{18}$ 1.7 uM; Injection volume: 25 μL; Tray temp: 10° C.; Column oven temp: 45° C.; MS run time: 60 minutes; Divert valve: none

TABLE 2

Gradient for 35% fraction

| No | Time | A % | B % | C % | D % | μL/min |
|---|---|---|---|---|---|---|
| 1 | 0 | 100 | 0 | 0 | 0 | 300 |
| 2 | 5 | 100 | 0 | 0 | 0 | 300 |
| 3 | 45 | 50 | 50 | 0 | 0 | 300 |
| 4 | 46 | 100 | 0 | 0 | 0 | 300 |
| 5 | 60 | 100 | 0 | 0 | 0 | 300 |

TABLE 3

Gradient for 65% fraction

| No | Time | A % | B % | C % | D % | μL/min |
|---|---|---|---|---|---|---|
| 1 | 0 | 70 | 30 | 0 | 0 | 300 |
| 2 | 5 | 70 | 30 | 0 | 0 | 300 |
| 3 | 45 | 25 | 75 | 0 | 0 | 300 |
| 4 | 46 | 70 | 30 | 0 | 0 | 300 |
| 5 | 60 | 70 | 30 | 0 | 0 | 300 |

Mass Spectrometry Parameters and Methods

MS scan event 1: FTMS; resolution 30000; scan range 500.0-2000.0
MS scan event 2-6: ITMS + c norm Dep MS/MS $1^{st}$, $2^{nd}$, $3^{rd}$ most intense ion from scan 1 for differential expression and from list for targeted identification
    Activation Type: CID
    Min Signal Required: 500
    Isolation Width: 1.5
    Normalized Coll. Energy: 35.0
    Default Charge State: 2
    Activation Q: 0.250
    Activation Time: 30.000
    CV = 0.0 V
Data Dependent Settings for differential expression:
    Use separate polarity settings disabled
    Parent Mass List: none
    Reject Mass List: none
    Neutral loss Mass List: none
    Product Mass List: none
    Neutral loss in top: 3
    Product in top: 3
    Most intense if no parent masses found not enabled
    Add/subtract mass not enabled
    FT master scan preview mode enabled
    Charge state screening enabled
    Monoisotopic precursor selection enabled
    Non-peptide monoisotopic recognition not enabled
    Charge state rejection enabled
        Unassigned charge states: rejected
        Charge state 1: not rejected
        Charge state 2: not rejected
        Charge state 3: not rejected
        Charge state 4+: not rejected
Data Dependent Settings for targeted identification:
    Use separate polarity settings disabled
    Reject Mass List: none
    Neutral loss Mass List: none
    Product Mass List: none
    Neutral loss in top: 3

-continued

```
        Product in top: 3
        Most intense if no parent masses found not enabled
        Add/subtract mass not enabled
        FT master scan preview mode enabled
        Charge state screening enabled
        Monoisotopic precursor selection enabled
        Non-peptide monoisotopic recognition not enabled
        Charge state rejection enabled
                Unassigned charge states: rejected
                Charge state 1: not rejected
                Charge state 2: not rejected
                Charge state 3: not rejected
                Charge state 4+: not rejected
Global Data Dependent Settings"
        Use global parent and reject mass lists not enabled for
        differential expression and enabled for targeted identification
        Exclude parent mass from data dependent selection not
enabled
        Exclusion mass width relative to mass
        Exclusion mass width relative to low (ppm): 20.00
        Exclusion mass width relative to high (ppm): 20.00
        Parent mass width relative to mass
        Parent mass width low (ppm): 10.00
        Parent mass width high (ppm): 10.00
        Reject mass width relative to mass
        Reject mass width low (ppm): 20.00
        Reject mass width high (ppm): 20.00
        Zoom/UltraZoom scan mass width by mass
        Zoom/UltraZoom scan mass low: 5.00
        Zoom/UltraZoom scan mass high: 5.00
        FT SIM scan mass width low: 5.00
        FT SIM scan mass width high: 5.00
        Neutral Loss candidates processed by decreasing intensity
        Neutral loss mass width by mass
        Neutral Loss mass width low: 0.50000
        Neutral Loss mass width high: 0.50000
        Product candidates processed by decreasing intensity
        Product mass width by mass
        Product mass width low: 0.50000
        Product mass width high: 0.50000
        MS mass range: 0.00-1000000.00
        Use m/z values as masses not enabled
        Analog UV data dep. Not enabled
        Dynamic exclusion enabled
                Repeat Count: 2
                Repeat Duration: 30.00
                Exclusion List Size: 500
                Exclusion Duration: 60.00
                Exclusion mass width relative to mass
                Exclusion mass width low (ppm): 20.00
                Exclusion mass width high (ppm): 20.00
        Isotopic data dependence not enabled
        Mass Tags data dependence not enabled
        Custom Data Dependent Settings not enabled
MS Tune File Values
Source Type: ESI
Capillary Temp (° C.): 250.00
Sheath gas Flow: 24.00
Aux Gas Flow: 13.00
Sweep Gas Flow: 0
Ion Trap MSn AGC Target: 10000
FTMS Injection waveforms: off
FTMS AGC Target: 500000
Source voltage (kV): 4.50
Source current (µA): 100.00
Capillary Voltage (V): 68.28
Tube Lens (V): 130.00
Skimmer Offset (V): 0.00
Multipole RF Amplifier (Vp-p): 550.00
Multipole 00 offset (V): −1.60
Lens 0 Voltage (V): −2.70
Multipole 0 offset (V): −5.80
Lens 1 Voltage (V): −11.00
Gate Lens offset (V): −60.00
Multipole 1 offset (V): −10.50
Front Lens (V): −5.18
FTMS full microscans: 1
FTMS full Max Ion Time (ms): 500
Ion Trap MSn Micro Scans: 3
Ion Trap MSn Max Ion Time: 100
```

The mass spec data from the above analysis were analyzed for differential expression of the peptides using SIEVE 1.3 software with the following parameters:

TABLE 4

| SIEVE Parameters | |
| --- | --- |
| Alignment Parameters | |
| AlignmentBypass | False |
| CorrelationBinWidth | 1 |
| RT LimitsForAlignment | True |
| TileIncrement | 150 |
| TileMaximum | 300 |
| TileSize | 300 |
| Tile Threshold | 0.6 |
| Analysis Definition | |
| Experiment Target | PROTEOMICS |
| Experiment Type | AVSB |
| Frame Parameters | |
| AvgChargeProcessor | False |
| ControlGroup | c |
| FrameIDCriteria | ORDER BY PVALUE ASC |
| FrameSeedFile | |
| KMClusters | 10 |
| MS2CorrProcessor | False |
| MZStart | 500 |
| MZStop | 2000 |
| MZWidth | 0.01 |
| ProcessorModules | PCA V1.0:ROC V1.0 |
| RTStart | 0 |
| RTStop | 59.98 |
| RTWidth | 1.5 |
| UseTICNormalizedRatios | False |

TABLE 5

Global Parent mass 35% fraction for targeted identification:

| m/z | start time (min) | End time (min) |
| --- | --- | --- |
| 500.837 | 20.8 | 21.4 |
| 511.557 | 20.8 | 21.4 |
| 516.216 | 20.8 | 21.4 |
| 529.195 | 20.8 | 21.4 |
| 534.519 | 20.8 | 21.4 |
| 540.878 | 23.4 | 24.0 |
| 549.959 | 44.1 | 44.7 |
| 554.519 | 22.1 | 22.7 |
| 586.686 | 23.3 | 23.9 |
| 588.915 | 20.8 | 21.4 |
| 590.986 | 44.1 | 44.7 |
| 596.798 | 20.7 | 21.3 |
| 630.336 | 26.0 | 26.6 |
| 632.392 | 37.0 | 37.6 |
| 640.314 | 20.8 | 21.4 |
| 646.067 | 17.9 | 18.5 |
| 661.491 | 35.0 | 35.6 |
| 662.294 | 27.1 | 27.7 |
| 666.330 | 37.3 | 37.9 |
| 666.770 | 20.8 | 21.4 |
| 697.336 | 20.7 | 21.3 |
| 697.837 | 20.7 | 21.3 |
| 714.396 | 27.1 | 27.7 |
| 722.599 | 20.7 | 21.3 |
| 732.085 | 20.7 | 21.3 |
| 736.079 | 20.7 | 21.3 |

TABLE 5-continued

Global Parent mass 35% fraction for targeted identification:

| m/z | start time (min) | End time (min) |
|---|---|---|
| 745.375 | 28.8 | 29.4 |
| 747.859 | 20.7 | 21.3 |
| 748.299 | 20.8 | 21.4 |
| 746.279 | 22.5 | 23.1 |
| 758.347 | 20.8 | 21.4 |
| 761.089 | 20.8 | 21.4 |
| 762.952 | 33.1 | 33.7 |
| 766.832 | 20.8 | 21.4 |
| 770.824 | 20.8 | 21.4 |
| 774.316 | 20.8 | 21.4 |
| 785.495 | 37.0 | 37.6 |
| 792.484 | 37.0 | 37.6 |
| 798.662 | 27.1 | 27.7 |
| 815.324 | 23.7 | 24.3 |
| 815.292 | 22.0 | 22.6 |
| 831.276 | 22.0 | 22.6 |
| 845.270 | 27.1 | 27.7 |
| 857.071 | 27.1 | 27.7 |
| 883.346 | 36.5 | 37.1 |
| 888.005 | 20.8 | 21.4 |
| 908.015 | 20.8 | 21.4 |
| 926.783 | 21.2 | 21.8 |
| 929.445 | 20.7 | 21.3 |
| 946.081 | 37.0 | 37.6 |
| 963.128 | 20.7 | 21.3 |
| 972.536 | 37.0 | 37.6 |
| 980.768 | 20.7 | 21.3 |
| 996.811 | 20.7 | 21.3 |
| 999.409 | 20.7 | 21.3 |
| 1014.449 | 20.8 | 21.4 |
| 1017.377 | 39.7 | 40.3 |
| 1017.250 | 39.6 | 40.2 |
| 1034.163 | 36.5 | 37.1 |
| 1061.032 | 38.0 | 38.6 |
| 1071.011 | 20.7 | 21.3 |
| 1073.287 | 38.3 | 38.9 |
| 1074.429 | 43.6 | 44.2 |
| 1075.546 | 43.0 | 43.6 |
| 1078.177 | 40.3 | 40.9 |
| 1083.736 | 22.1 | 22.7 |
| 1089.401 | 38.0 | 38.6 |
| 1096.026 | 20.7 | 21.3 |
| 1101.960 | 43.0 | 43.6 |
| 1104.411 | 37.4 | 38.0 |
| 1109.504 | 20.7 | 21.3 |
| 1117.566 | 42.9 | 43.5 |
| 1141.310 | 40.2 | 40.8 |
| 1140.059 | 40.2 | 40.8 |
| 1162.715 | 39.6 | 40.2 |
| 1162.285 | 39.6 | 40.2 |
| 1175.385 | 42.8 | 43.4 |
| 1175.963 | 20.7 | 21.3 |
| 1182.040 | 36.5 | 37.1 |
| 1185.065 | 38.6 | 39.2 |
| 1184.315 | 38.7 | 39.3 |
| 1184.044 | 36.5 | 37.1 |
| 1186.945 | 20.7 | 21.3 |
| 1189.456 | 36.5 | 37.1 |
| 1197.564 | 38.3 | 38.9 |
| 1201.052 | 38.0 | 38.6 |
| 1205.551 | 27.1 | 27.7 |
| 1221.832 | 38.1 | 38.7 |
| 1221.330 | 38.0 | 38.6 |
| 1221.956 | 38.1 | 38.7 |
| 1221.203 | 38.0 | 38.6 |
| 1229.059 | 41.7 | 42.3 |
| 1229.337 | 43.0 | 43.6 |
| 1234.050 | 43.3 | 43.9 |
| 1234.184 | 43.2 | 43.8 |
| 1237.197 | 38.1 | 38.7 |
| 1239.714 | 38.3 | 38.9 |
| 1239.903 | 40.3 | 40.9 |
| 1239.906 | 22.0 | 22.6 |
| 1239.336 | 39.3 | 39.9 |
| 1241.893 | 22.0 | 22.6 |
| 1245.780 | 42.9 | 43.5 |
| 1244.893 | 41.7 | 42.3 |
| 1244.821 | 38.2 | 38.8 |
| 1252.485 | 42.9 | 43.5 |
| 1253.180 | 38.0 | 38.6 |
| 1262.757 | 41.7 | 42.3 |
| 1269.226 | 43.0 | 43.6 |
| 1268.942 | 42.9 | 43.5 |
| 1271.795 | 41.7 | 42.3 |
| 1271.940 | 41.7 | 42.3 |
| 1272.223 | 41.7 | 42.3 |
| 1271.511 | 41.7 | 42.3 |
| 1271.366 | 41.5 | 42.1 |
| 1271.653 | 43.6 | 44.2 |
| 1271.939 | 42.9 | 43.5 |
| 1271.663 | 43.0 | 43.6 |
| 1279.356 | 41.7 | 42.3 |
| 1279.640 | 41.7 | 42.3 |
| 1280.487 | 43.1 | 43.7 |
| 1282.341 | 42.9 | 43.5 |
| 1282.623 | 42.9 | 43.5 |
| 1283.501 | 41.7 | 42.3 |
| 1283.215 | 41.7 | 42.3 |
| 1287.661 | 42.8 | 43.4 |
| 1287.380 | 42.8 | 43.4 |
| 1287.671 | 42.9 | 43.5 |
| 1289.949 | 41.4 | 42.0 |
| 1290.093 | 41.4 | 42.0 |
| 1290.231 | 41.4 | 42.0 |
| 1295.514 | 42.8 | 43.4 |
| 1302.780 | 40.2 | 40.8 |
| 1313.671 | 42.8 | 43.4 |
| 1326.085 | 42.9 | 43.5 |
| 1329.279 | 41.4 | 42.0 |
| 1340.257 | 42.8 | 43.4 |
| 1353.504 | 38.6 | 39.2 |
| 1353.226 | 38.0 | 38.6 |
| 1354.345 | 38.0 | 38.6 |
| 1355.998 | 39.6 | 40.2 |
| 1361.344 | 38.6 | 39.2 |
| 1378.833 | 43.0 | 43.6 |
| 1393.662 | 20.7 | 21.3 |
| 1395.947 | 38.0 | 38.6 |
| 1395.808 | 38.1 | 38.7 |
| 1396.095 | 38.0 | 38.6 |
| 1396.238 | 38.1 | 38.7 |
| 1403.093 | 38.1 | 38.7 |
| 1405.390 | 37.0 | 37.6 |
| 1412.808 | 42.9 | 43.5 |
| 1416.957 | 38.2 | 38.8 |
| 1417.242 | 38.2 | 38.8 |
| 1416.813 | 38.2 | 38.8 |
| 1415.521 | 38.3 | 38.9 |
| 1416.365 | 38.2 | 38.8 |
| 1423.711 | 43.0 | 43.6 |
| 1432.054 | 43.1 | 43.7 |
| 1434.534 | 38.3 | 38.9 |
| 1444.691 | 20.7 | 21.3 |
| 1461.219 | 39.3 | 39.9 |
| 1466.392 | 38.3 | 38.9 |
| 1480.934 | 43.0 | 43.6 |
| 1480.763 | 42.9 | 43.5 |
| 1483.434 | 41.5 | 42.1 |
| 1483.261 | 41.5 | 42.1 |
| 1483.594 | 43.1 | 43.7 |
| 1483.096 | 41.5 | 42.1 |
| 1488.084 | 41.5 | 42.1 |
| 1488.253 | 41.5 | 42.1 |
| 1492.580 | 41.8 | 42.4 |
| 1492.738 | 43.1 | 43.7 |
| 1494.710 | 20.7 | 21.3 |
| 1493.188 | 41.4 | 42.0 |
| 1501.262 | 43.1 | 43.7 |

TABLE 5-continued

Global Parent mass 35% fraction for targeted identification:

| m/z | start time (min) | End time (min) |
|---|---|---|
| 1501.243 | 42.8 | 43.4 |
| 1504.607 | 41.4 | 42.0 |
| 1519.408 | 40.2 | 40.8 |
| 1519.963 | 42.8 | 43.4 |
| 1533.454 | 41.4 | 42.0 |
| 1550.589 | 42.9 | 43.5 |
| 1567.262 | 43.0 | 43.6 |
| 1566.964 | 43.2 | 43.8 |
| 1616.809 | 42.8 | 43.4 |
| 1625.276 | 38.1 | 38.7 |
| 1682.802 | 41.4 | 42.0 |
| 1708.700 | 35.2 | 35.8 |
| 1715.693 | 43.0 | 43.6 |
| 1719.490 | 42.8 | 43.4 |
| 1720.363 | 43.1 | 43.7 |
| 1720.076 | 41.7 | 42.3 |
| 1735.925 | 42.9 | 43.5 |
| 1735.448 | 42.9 | 43.5 |
| 1742.423 | 42.8 | 43.4 |
| 1742.691 | 39.3 | 39.9 |
| 1749.090 | 42.8 | 43.4 |
| 1755.091 | 42.9 | 43.5 |
| 1766.811 | 43.0 | 43.6 |
| 1769.294 | 42.9 | 43.5 |
| 1775.798 | 43.0 | 43.6 |
| 1802.490 | 42.8 | 43.4 |
| 1808.484 | 42.9 | 43.5 |
| 1822.120 | 41.4 | 42.0 |
| 1893.263 | 5.0 | 60.0 |
| 1796.466 | 5.0 | 60.0 |
| 1596.971 | 5.0 | 60.0 |
| 1368.976 | 5.0 | 60.0 |
| 1150.101 | 5.0 | 60.0 |
| 1635.848 | 5.0 | 60.0 |
| 1338.604 | 5.0 | 60.0 |
| 921.201 | 5.0 | 60.0 |
| 775.405 | 5.0 | 60.0 |
| 1618.973 | 5.0 | 60.0 |
| 1324.797 | 5.0 | 60.0 |
| 1121.137 | 5.0 | 60.0 |
| 911.113 | 5.0 | 60.0 |
| 809.990 | 5.0 | 60.0 |
| 1529.751 | 5.0 | 60.0 |
| 1384.157 | 5.0 | 60.0 |
| 1263.883 | 5.0 | 60.0 |
| 1211.263 | 5.0 | 60.0 |
| 1162.853 | 5.0 | 60.0 |
| 1247.480 | 5.0 | 60.0 |
| 1366.192 | 5.0 | 60.0 |
| 1510.899 | 5.0 | 60.0 |
| 1950.616 | 5.0 | 60.0 |
| 1540.172 | 5.0 | 60.0 |
| 1170.773 | 5.0 | 60.0 |
| 1090.293 | 5.0 | 60.0 |
| 1185.014 | 5.0 | 60.0 |
| 1362.615 | 5.0 | 60.0 |
| 1542.070 | 5.0 | 60.0 |
| 1445.754 | 5.0 | 60.0 |
| 1360.769 | 5.0 | 60.0 |
| 1285.227 | 5.0 | 60.0 |
| 1217.636 | 5.0 | 60.0 |
| 1156.805 | 5.0 | 60.0 |
| 1101.767 | 5.0 | 60.0 |
| 1051.732 | 5.0 | 60.0 |
| 1006.048 | 5.0 | 60.0 |
| 964.172 | 5.0 | 60.0 |
| 14138.386 | 5.0 | 60.0 |
| 1768.180 | 5.0 | 60.0 |
| 1286.224 | 5.0 | 60.0 |
| 1088.498 | 5.0 | 60.0 |
| 943.499 | 5.0 | 60.0 |
| 884.593 | 5.0 | 60.0 |
| 786.924 | 5.0 | 60.0 |
| 745.080 | 5.0 | 60.0 |
| 954.251 | 5.0 | 60.0 |
| 1040.909 | 5.0 | 60.0 |
| 1144.899 | 5.0 | 60.0 |
| 1205.104 | 5.0 | 60.0 |
| 1526.197 | 5.0 | 60.0 |
| 1430.872 | 5.0 | 60.0 |
| 1907.494 | 5.0 | 60.0 |
| 1760.841 | 5.0 | 60.0 |
| 1977.132 | 5.0 | 60.0 |
| 1757.527 | 5.0 | 60.0 |
| 1581.907 | 5.0 | 60.0 |
| 1438.189 | 5.0 | 60.0 |
| 1054.941 | 5.0 | 60.0 |
| 879.285 | 5.0 | 60.0 |
| 659.716 | 5.0 | 60.0 |
| 1897.745 | 5.0 | 60.0 |
| 1660.653 | 5.0 | 60.0 |
| 1022.328 | 5.0 | 60.0 |
| 633.253 | 5.0 | 60.0 |
| 1831.242 | 5.0 | 60.0 |
| 1664.857 | 5.0 | 60.0 |
| 1526.203 | 5.0 | 60.0 |
| 1408.880 | 5.0 | 60.0 |
| 1308.318 | 5.0 | 60.0 |
| 796.762 | 5.0 | 60.0 |
| 733.101 | 5.0 | 60.0 |
| 1991.952 | 5.0 | 60.0 |
| 1770.739 | 5.0 | 60.0 |
| 1593.766 | 5.0 | 60.0 |
| 1448.969 | 5.0 | 60.0 |
| 1328.306 | 5.0 | 60.0 |
| 1226.206 | 5.0 | 60.0 |
| 1138.692 | 5.0 | 60.0 |
| 1062.846 | 5.0 | 60.0 |
| 996.481 | 5.0 | 60.0 |
| 937.924 | 5.0 | 60.0 |
| 885.873 | 5.0 | 60.0 |
| 839.301 | 5.0 | 60.0 |
| 797.909 | 5.0 | 60.0 |
| 759.464 | 5.0 | 60.0 |
| 724.988 | 5.0 | 60.0 |
| 693.511 | 5.0 | 60.0 |
| 664.657 | 5.0 | 60.0 |
| 638.111 | 5.0 | 60.0 |
| 1427.610 | 5.0 | 60.0 |
| 1223.810 | 5.0 | 60.0 |
| 1070.959 | 5.0 | 60.0 |
| 856.969 | 5.0 | 60.0 |
| 779.154 | 5.0 | 60.0 |
| 782.314 | 5.0 | 60.0 |
| 626.056 | 5.0 | 60.0 |
| 1042.755 | 5.0 | 60.0 |
| 1037.510 | 5.0 | 60.0 |
| 692.009 | 5.0 | 60.0 |
| 519.259 | 5.0 | 60.0 |
| 1291.643 | 5.0 | 60.0 |
| 861.431 | 5.0 | 60.0 |
| 646.325 | 5.0 | 60.0 |
| 1480.558 | 5.0 | 60.0 |
| 905.177 | 5.0 | 60.0 |
| 857.589 | 5.0 | 60.0 |
| 1394.901 | 5.0 | 60.0 |
| 761.313 | 5.0 | 60.0 |
| 1104.010 | 5.0 | 60.0 |
| 631.727 | 5.0 | 60.0 |
| 883.410 | 5.0 | 60.0 |
| 1768.860 | 5.0 | 60.0 |
| 708.148 | 5.0 | 60.0 |
| 590.291 | 5.0 | 60.0 |
| 785.635 | 5.0 | 60.0 |
| 845.991 | 5.0 | 60.0 |
| 916.407 | 5.0 | 60.0 |
| 999.625 | 5.0 | 60.0 |
| 1221.540 | 5.0 | 60.0 |

TABLE 5-continued

Global Parent mass 35% fraction for targeted identification:

| m/z | start time (min) | End time (min) |
|---|---|---|
| 1831.806 | 5.0 | 60.0 |
| 1615.749 | 5.0 | 60.0 |
| 1243.116 | 5.0 | 60.0 |
| 1077.502 | 5.0 | 60.0 |
| 950.855 | 5.0 | 60.0 |
| 850.871 | 5.0 | 60.0 |
| 1177.032 | 5.0 | 60.0 |
| 969.498 | 5.0 | 60.0 |
| 1098.630 | 5.0 | 60.0 |
| 1862.260 | 5.0 | 60.0 |
| 1676.135 | 5.0 | 60.0 |
| 1289.567 | 5.0 | 60.0 |
| 1117.759 | 5.0 | 60.0 |
| 882.653 | 5.0 | 60.0 |
| 1480.757 | 5.0 | 60.0 |
| 1253.103 | 5.0 | 60.0 |
| 1018.335 | 5.0 | 60.0 |
| 905.299 | 5.0 | 60.0 |
| 1472.097 | 5.0 | 60.0 |
| 1104.325 | 5.0 | 60.0 |
| 1766.315 | 5.0 | 60.0 |
| 883.661 | 5.0 | 60.0 |
| 679.972 | 5.0 | 60.0 |
| 589.443 | 5.0 | 60.0 |
| 1809.590 | 5.0 | 60.0 |
| 1357.444 | 5.0 | 60.0 |
| 1086.157 | 5.0 | 60.0 |
| 958.492 | 5.0 | 60.0 |
| 857.704 | 5.0 | 60.0 |
| 1286.224 | 5.0 | 60.0 |
| 1768.180 | 5.0 | 60.0 |
| 1571.827 | 5.0 | 60.0 |
| 1414.745 | 5.0 | 60.0 |
| 1179.883 | 5.0 | 60.0 |

TABLE 6

| MZ | Start Time | End Time |
|---|---|---|
| 747.8585 | 20.963 | 21.963 |
| 748.3594 | 20.963 | 21.963 |
| 1494.711 | 20.973 | 21.973 |
| 1393.662 | 20.925 | 21.925 |
| 997.1431 | 20.963 | 21.963 |
| 1091.809 | 43.558 | 44.558 |
| 758.9495 | 23.687 | 24.687 |
| 963.4607 | 20.963 | 21.963 |
| 996.8089 | 20.963 | 21.963 |
| 529.4085 | 20.079 | 21.079 |
| 963.1265 | 20.963 | 21.963 |
| 1495.694 | 21.586 | 22.586 |
| 939.1018 | 37.446 | 38.446 |
| 785.4966 | 37.446 | 38.446 |
| 1279.621 | 20.973 | 21.973 |
| 938.6002 | 37.446 | 38.446 |
| 632.3923 | 37.449 | 38.449 |
| 692.862 | 27.718 | 28.718 |
| 1245.308 | 37.446 | 38.446 |
| 713.5975 | 24.835 | 25.835 |
| 766.8335 | 20.973 | 21.973 |
| 1118.573 | 18.91 | 19.91 |
| 1356.332 | 40.142 | 41.142 |
| 713.2632 | 24.862 | 25.862 |
| 632.8939 | 37.449 | 38.449 |
| 767.3351 | 20.973 | 21.973 |
| 1245.354 | 45.921 | 46.921 |
| 1092.202 | 37.164 | 38.164 |
| 1091.703 | 37.446 | 38.446 |
| 576.0089 | 45.797 | 46.797 |
| 774.3157 | 20.963 | 21.963 |
| 1398.409 | 37.446 | 38.446 |
| 1082.377 | 29.745 | 30.745 |
| 1082.521 | 29.72 | 30.72 |
| 747.7883 | 28.871 | 29.871 |
| 747.5877 | 28.871 | 29.871 |
| 1017.626 | 40.143 | 41.143 |
| 856.5498 | 27.091 | 28.091 |
| 1082.234 | 29.745 | 30.745 |
| 923.815 | 27.718 | 28.718 |
| 514.3178 | 45.805 | 46.805 |
| 670.3671 | 22.036 | 23.036 |
| 1185.613 | 29.438 | 30.438 |
| 534.9825 | 45.819 | 46.819 |
| 520.341 | 45.691 | 46.691 |
| 747.9889 | 28.871 | 29.871 |
| 886.6 | 30.939 | 31.939 |
| 1262.604 | 29.769 | 30.769 |
| 723.3659 | 32.732 | 33.732 |
| 994.2356 | 45.096 | 46.096 |

TABLE 7

Global Parent Masses 65% fraction for targeted identification

| m/z | Start time (min) | End time (min) |
|---|---|---|
| 1222.77185 | 18.898 | 19.498 |
| 1222.62903 | 18.898 | 19.498 |
| 1222.91467 | 18.898 | 19.498 |
| 1222.48633 | 18.898 | 19.498 |
| 1222.34363 | 18.898 | 19.498 |
| 535.41309 | 44.458 | 45.058 |
| 549.31537 | 35.307 | 35.907 |
| 1240.9231 | 18.895 | 19.495 |
| 1241.21008 | 18.895 | 19.495 |
| 522.59802 | 47.752 | 48.352 |
| 500.20343 | 24.938 | 25.538 |
| 557.44525 | 34.845 | 35.445 |
| 700.55261 | 44.458 | 45.058 |
| 502.29593 | 31.133 | 31.733 |
| 576.00928 | 20.109 | 20.709 |
| 1229.77344 | 19.099 | 19.699 |
| 1227.05896 | 21.087 | 21.687 |
| 666.32935 | 12.86 | 13.46 |
| 555.42859 | 44.458 | 45.058 |
| 919.62494 | 10.837 | 11.437 |
| 1086.43494 | 18.895 | 19.495 |
| 500.20352 | 24.16 | 24.76 |
| 785.54749 | 44.458 | 45.058 |
| 1240.49377 | 18.893 | 19.493 |
| 656.32324 | 35.678 | 36.278 |
| 576.00928 | 20.962 | 21.562 |
| 1044.64368 | 33.755 | 34.355 |
| 565.43127 | 34.845 | 35.445 |
| 534.98254 | 20.109 | 20.709 |
| 689.45453 | 33.647 | 34.247 |
| 522.59821 | 46.986 | 47.586 |
| 552.97772 | 35.36 | 35.96 |
| 1160.28918 | 18.176 | 18.776 |
| 535.41296 | 40.034 | 40.634 |
| 514.31842 | 22.557 | 23.157 |
| 1092.1864 | 19.016 | 19.616 |
| 1226.62988 | 21.087 | 21.687 |
| 1245.21155 | 21.073 | 21.673 |
| 538.27802 | 31.183 | 31.783 |
| 595.95276 | 20.109 | 20.709 |
| 770.53705 | 35.665 | 36.265 |
| 514.13129 | 22.572 | 23.172 |
| 533.19391 | 45.359 | 45.959 |
| 503.29941 | 31.133 | 31.733 |
| 1035.65649 | 33.8 | 34.4 |
| 1228.77197 | 19.099 | 19.699 |

TABLE 7-continued

Global Parent Masses 65% fraction for targeted identification

| m/z | Start time (min) | End time (min) |
|---|---|---|
| 865.69196 | 44.492 | 45.092 |
| 552.64246 | 35.36 | 35.96 |
| 621.2735 | 35.307 | 35.907 |
| 639.38116 | 12.36 | 12.96 |
| 795.98547 | 12.411 | 13.011 |
| 788.02655 | 34.697 | 35.297 |
| 816.57715 | 46.757 | 47.357 |
| 1245.06909 | 21.073 | 21.673 |
| 590.78833 | 35.36 | 35.96 |
| 522.59857 | 46.026 | 46.626 |
| 1089.55884 | 16.803 | 17.403 |
| 785.59174 | 41.855 | 42.455 |
| 656.03418 | 44.963 | 45.563 |
| 1245.64099 | 21.073 | 21.673 |
| 734.5838 | 41.312 | 41.912 |
| 527.42432 | 44.458 | 45.058 |
| 816.57703 | 45.912 | 46.512 |
| 564.90961 | 44.767 | 45.367 |
| 1160.14612 | 18.176 | 18.776 |
| 787.98962 | 33.811 | 34.411 |
| 1530.9856 | 33.8 | 34.4 |
| 834.60272 | 45.536 | 46.136 |
| 1013.6778 | 47.807 | 48.407 |
| 927.50275 | 24.16 | 24.76 |
| 770.53809 | 41.117 | 41.717 |
| 672.8623 | 20.478 | 21.078 |
| 1236.03796 | 18.898 | 19.498 |
| 827.44568 | 17.482 | 18.082 |
| 1021.62933 | 31.226 | 31.826 |
| 612.2973 | 35.687 | 36.287 |
| 818.59338 | 40.929 | 41.529 |
| 763.073 | 44.933 | 45.533 |
| 884.26294 | 15.568 | 16.168 |
| 784.58783 | 34.201 | 34.801 |
| 647.50586 | 43.805 | 44.405 |
| 816.57739 | 42.456 | 43.056 |
| 816.57806 | 44.856 | 45.456 |
| 589.98645 | 20.109 | 20.709 |
| 678.38123 | 29.773 | 30.373 |
| 574.37909 | 36.07 | 36.67 |
| 590.789 | 33.644 | 34.244 |
| 550.38953 | 39.608 | 40.208 |
| 1234.76331 | 21.088 | 21.688 |
| 747.63464 | 45.81 | 46.41 |
| 684.06628 | 43.942 | 44.542 |
| 834.60327 | 43.684 | 44.284 |
| 1226.48657 | 21.087 | 21.687 |
| 537.77429 | 31.183 | 31.783 |
| 726.76282 | 35.307 | 35.907 |
| 575.44519 | 44.421 | 45.021 |
| 856.57281 | 44.856 | 45.456 |
| 818.56958 | 41.989 | 42.589 |
| 818.59167 | 37.061 | 37.661 |
| 780.55658 | 44.856 | 45.456 |
| 783.59045 | 45.191 | 45.791 |
| 806.57233 | 36.618 | 37.218 |
| 547.08124 | 12.898 | 13.498 |
| 1255.62939 | 19.003 | 19.603 |
| 1101.73071 | 47.659 | 48.259 |
| 616.12958 | 24.863 | 25.463 |
| 942.46729 | 24.16 | 24.76 |
| 1065.6875 | 33.644 | 34.244 |
| 564.9295 | 35.766 | 36.366 |
| 1096.42273 | 16.828 | 17.428 |
| 816.57843 | 43.658 | 44.258 |
| 747.63562 | 42.131 | 42.731 |
| 606.30951 | 33.644 | 34.244 |
| 809.47382 | 43.611 | 44.211 |
| 1255.79785 | 12.391 | 12.991 |
| 868.50171 | 39.152 | 39.752 |
| 1234.90649 | 21.088 | 21.688 |
| 789.95789 | 31.226 | 31.826 |
| 576.27594 | 35.36 | 35.96 |
| 799.41437 | 15.568 | 16.168 |
| 528.29279 | 35.166 | 35.766 |
| 842.56836 | 45.191 | 45.791 |
| 1081.91406 | 18.898 | 19.498 |
| 1865.21143 | 12.45 | 13.05 |
| 536.73425 | 10.897 | 11.497 |
| 800.58289 | 44.856 | 45.456 |
| 1761.11316 | 33.8 | 34.4 |
| 1234.33362 | 21.088 | 21.688 |
| 523.28363 | 46.596 | 47.196 |
| 692.56415 | 44.492 | 45.092 |
| 856.57227 | 44.038 | 44.638 |
| 682.36548 | 42.931 | 43.531 |
| 584.9256 | 45.702 | 46.302 |
| 508.58325 | 47.575 | 48.175 |
| 549.30127 | 31.216 | 31.816 |
| 547.81464 | 35.36 | 35.96 |
| 640.4176 | 34.467 | 35.067 |
| 874.50842 | 12.645 | 13.245 |
| 1089.43811 | 21.069 | 21.669 |
| 834.58734 | 44.106 | 44.706 |
| 548.95966 | 20.109 | 20.709 |
| 811.67133 | 44.9 | 45.5 |
| 977.78485 | 43.805 | 44.405 |
| 984.71124 | 45.034 | 45.634 |
| 816.57745 | 39.918 | 40.518 |
| 541.35706 | 37.363 | 37.963 |
| 1242.32043 | 21.087 | 21.687 |
| 1296.89185 | 18.895 | 19.495 |
| 816.57672 | 41.217 | 41.817 |
| 834.60321 | 42.206 | 42.806 |
| 800.58289 | 36.618 | 37.218 |
| 1057.11133 | 31.226 | 31.826 |
| 841.43475 | 46.467 | 47.067 |
| 1090.30103 | 18.898 | 19.498 |
| 1076.55383 | 19.11 | 19.71 |
| 516.23901 | 44.751 | 45.351 |
| 699.44244 | 34.996 | 35.596 |
| 1082.91907 | 19.11 | 19.71 |
| 816.57849 | 36.279 | 36.879 |
| 1073.30225 | 21.087 | 21.687 |
| 836.44843 | 35.316 | 35.916 |
| 928.77789 | 43.805 | 44.405 |
| 500.30814 | 33.647 | 34.247 |
| 1096.2981 | 16.79 | 17.39 |
| 1252.44897 | 19.099 | 19.699 |
| 800.5827 | 37.369 | 37.969 |
| 797.4433 | 31.183 | 31.783 |
| 780.55627 | 41.566 | 42.166 |
| 997.70264 | 47.786 | 48.386 |
| 1207.7627 | 18.983 | 19.583 |
| 847.11377 | 44.569 | 45.169 |
| 1512.69934 | 18.898 | 19.498 |
| 1856.21155 | 12.469 | 13.069 |
| 1250.02783 | 19.099 | 19.699 |
| 1095.60803 | 33.811 | 34.411 |
| 658.4317 | 36.611 | 37.211 |
| 1098.92664 | 19.016 | 19.616 |
| 972.04376 | 11.007 | 11.607 |
| 571.61591 | 31.37 | 31.97 |
| 561.2981 | 31.327 | 31.927 |
| 591.93182 | 39.863 | 40.463 |
| 800.58289 | 39.551 | 40.151 |
| 1309.29358 | 31.226 | 31.826 |
| 817.58173 | 41.855 | 42.455 |
| 650.42218 | 31.629 | 32.229 |
| 591.38416 | 35.266 | 35.866 |
| 550.34637 | 36.076 | 36.676 |
| 507.32535 | 32.394 | 32.994 |
| 1242.32202 | 19.128 | 19.728 |
| 1452.40747 | 16.828 | 17.428 |
| 640.44788 | 36.711 | 37.311 |
| 1296.60388 | 18.899 | 19.499 |
| 574.38922 | 39.095 | 39.695 |
| 1127.66003 | 35.36 | 35.96 |

TABLE 7-continued

Global Parent Masses 65% fraction for targeted identification

| m/z | Start time (min) | End time (min) |
|---|---|---|
| 549.04468 | 10.94 | 11.54 |
| 1288.52576 | 20.914 | 21.514 |
| 1452.41113 | 21.087 | 21.687 |
| 943.24799 | 33.642 | 34.242 |
| 1244.78503 | 21.069 | 21.669 |
| 1236.81531 | 12.778 | 13.378 |
| 656.0343 | 43.815 | 44.415 |
| 552.31799 | 33.644 | 34.244 |
| 533.19354 | 44.604 | 45.204 |
| 800.58374 | 38.715 | 39.315 |
| 800.58313 | 41.099 | 41.699 |
| 1105.16418 | 19.016 | 19.616 |
| 1080.5448 | 19.042 | 19.642 |
| 1234.19116 | 21.088 | 21.688 |
| 834.58575 | 37.992 | 38.592 |
| 722.05969 | 44.8 | 45.4 |
| 1537.02759 | 33.8 | 34.4 |
| 542.90161 | 44.569 | 45.169 |
| 1441.04272 | 18.895 | 19.495 |
| 1057.70325 | 34.656 | 35.256 |
| 575.38568 | 44.131 | 44.731 |
| 528.40558 | 36.809 | 37.409 |
| 694.05194 | 43.783 | 44.383 |
| 591.98376 | 21.656 | 22.256 |
| 780.55603 | 42.334 | 42.934 |
| 832.57202 | 40.929 | 41.529 |
| 708.03638 | 44.492 | 45.092 |
| 743.07135 | 41.312 | 41.912 |
| 731.60846 | 42.622 | 43.222 |
| 1350.76477 | 38.534 | 39.134 |
| 548.95728 | 33.799 | 34.399 |
| 816.57764 | 35.123 | 35.723 |
| 1080.66956 | 21.088 | 21.688 |
| 1063.85815 | 20.109 | 20.709 |
| 742.09894 | 35.339 | 35.939 |
| 527.31049 | 33.782 | 34.382 |
| 585.40204 | 33.044 | 33.644 |
| 859.44659 | 35.307 | 35.907 |
| 1080.41858 | 21.09 | 21.69 |
| 818.59222 | 34.562 | 35.162 |
| 1370.99316 | 44.806 | 45.406 |
| 1089.53223 | 19.11 | 19.71 |
| 1431.85144 | 12.411 | 13.011 |
| 695.89008 | 20.593 | 21.193 |
| 591.42761 | 41.789 | 42.389 |
| 504.75061 | 31.022 | 31.622 |
| 968.62842 | 39.552 | 40.152 |
| 863.56744 | 43.589 | 44.189 |
| 1439.88672 | 21.088 | 21.688 |
| 809.54089 | 40.947 | 41.547 |
| 1234.05066 | 21.049 | 21.649 |
| 1080.41943 | 19.099 | 19.699 |
| 1259.47473 | 20.829 | 21.429 |
| 1251.28943 | 12.43 | 13.03 |
| 1874.19434 | 12.428 | 13.028 |
| 1098.1825 | 12.403 | 13.003 |
| 678.40588 | 35.36 | 35.96 |
| 1080.2937 | 21.09 | 21.69 |
| 1163.60168 | 31.331 | 31.931 |
| 1081.90649 | 21.003 | 21.603 |
| 1303.35498 | 20.914 | 21.514 |
| 730.01355 | 37.502 | 38.102 |
| 540.86346 | 41.855 | 42.455 |
| 627.93677 | 39.175 | 39.775 |
| 1226.34363 | 21.087 | 21.687 |
| 754.50586 | 44.569 | 45.169 |
| 820.47766 | 35.368 | 35.968 |
| 1440.05261 | 21.087 | 21.687 |
| 763.05652 | 39.17 | 39.77 |
| 965.57751 | 35.3 | 35.9 |
| 956.92969 | 18.895 | 19.495 |
| 549.7619 | 33.862 | 34.462 |
| 1039.28918 | 32.404 | 33.004 |
| 1027.18225 | 38.565 | 39.165 |
| 540.86285 | 40.956 | 41.556 |
| 1220.05237 | 18.899 | 19.499 |
| 646.42871 | 33.65 | 34.25 |
| 1864.20129 | 12.391 | 12.991 |
| 1279.36121 | 18.902 | 19.502 |
| 1501.39685 | 18.898 | 19.498 |
| 1238.34937 | 20.516 | 21.116 |
| 1252.34387 | 20.983 | 21.583 |
| 1425.90979 | 33.836 | 34.436 |
| 1087.41003 | 19.128 | 19.728 |
| 1356.00232 | 16.785 | 17.385 |
| 804.55017 | 40.49 | 41.09 |
| 1611.92188 | 31.276 | 31.876 |
| 650.42383 | 33.647 | 34.247 |
| 1238.32214 | 17.718 | 18.318 |
| 795.48767 | 35.162 | 35.762 |
| 868.92645 | 31.353 | 31.953 |
| 1664.72192 | 12.411 | 13.011 |
| 1260.61768 | 21.069 | 21.669 |
| 1159.58667 | 46.467 | 47.067 |
| 741.53467 | 37.131 | 37.731 |
| 1266.21619 | 18.902 | 19.502 |
| 1275.7948 | 33.733 | 34.333 |
| 1245.63 | 20.983 | 21.583 |
| 696.51019 | 44.963 | 45.563 |
| 1089.3103 | 21.087 | 21.687 |
| 704.9386 | 43.649 | 44.249 |
| 1178.38953 | 35.3 | 35.9 |
| 811.95068 | 10.634 | 11.234 |
| 751.05286 | 44.8 | 45.4 |
| 936.49298 | 31.271 | 31.871 |
| 737.05133 | 44.458 | 45.058 |
| 939.39587 | 24.473 | 25.073 |
| 1027.66821 | 33.8 | 34.4 |
| 714.42725 | 39.557 | 40.157 |
| 780.98224 | 35.166 | 35.766 |
| 834.58661 | 41.639 | 42.239 |
| 571.37 | 39.418 | 40.018 |

TABLE 8

| MZ | Start Time | End Time |
|---|---|---|
| 502.2947 | 30.953 | 31.953 |
| 576.0092 | 17.85 | 18.85 |
| 1035.655 | 33.622 | 34.622 |
| 1021.629 | 31.026 | 32.026 |
| 787.9893 | 33.601 | 34.601 |
| 534.9822 | 17.85 | 18.85 |
| 1530.986 | 33.601 | 34.601 |
| 666.3301 | 12.673 | 13.673 |
| 789.9586 | 31.016 | 32.016 |
| 1027.67 | 33.601 | 34.601 |
| 1309.292 | 31.026 | 32.026 |
| 595.9525 | 17.85 | 18.85 |
| 780.982 | 35.033 | 36.033 |

Proteome Discoverer 1.1 was used to identify the differentially expressed peptides with the work flow as follows:

TABLE 9

Input Data

1. General Settings

| Precursor Selection | Use MS1 Precursor |
|---|---|

2. Spectrum Properties Filter

| Lower RT Limit | 5 |
|---|---|
| Upper RT Limit | 84 |

TABLE 9-continued

| Input Data | |
|---|---|
| Lowest Charge State | 1 |
| Highest Charge State | 4 |
| Min. Precursor Mass | 100 Da |
| Max. Precursor Mass | 9000 Da |
| Total Intensity Threshold | 0 |
| Minimum Peak Count | 1 |
| 3. Scan Event Filters | |
| Mass Analyzer | Is ITMS; FTMS |
| MS Order | Is MS2 |
| Activation Type | Is CID |
| Scan Type | Is Full |
| Ionization Source | Is ESI |
| Polarity Mode | Is + |
| 3. Peak Filters | |
| S/N Threshold | 0 |
| 4. Replacement for Unrecognized Properties | |
| Unrecognized Charge Re | 1; 2; 3; 4 |
| Unrecognized Mass Anal | ITMS |
| Unrecognized MS Order | MS2 |
| Unrecognized Activation | CID |
| Unrecognized Polarity | + |
| 1. Spectrum Match Criteria | |
| Precursor Mass Criterion | Same Measured M |
| Presursor Mass Tolerance | 7 ppm |
| Max. RT Difference [min] | 1.5 |
| Allow Mass Analyzer Mis | False |
| Allow MS Order Mismatch | False |
| 1. Thresholds | |
| S/N Threshold | 0 |
| 1. Filter Settings | |
| Mass Analyzer | Is ITMS; FTMS |
| MS Order | Is MS1; MS2 |
| Activation Type | Is CID |
| Scan Type | Is Full |
| Ionization Source | Is ESI |
| Polarity Mode | Is + |
| 1. Spectrum Properties | |
| Lowest Charge State | 1 |
| Highest Charge State | 4 |
| Min. Precursor Mass | 100 Da |
| Max. Precursor Mass | 9000 Da |
| 2. Thresholds | |
| Total Intensity Threshold | 0 |
| Minimum Peak Count | 1 |

TABLE 10

| 1. Input Data | |
|---|---|
| Protein Database | Maha.fasta |
| Enzyme Name | No-Enzyme [No |
| Maximum Missed Cleavage | 0 |
| 2. Decoy Database Search | |
| Search Against Decoy D | False |
| Target FDR (Strict) | 0.01 |
| Target FDR (Relaxed) | 0.05 |
| 3. Tolerances | |
| Precursor Mass Tolerance | 7 ppm |
| Fragment Mass Tolerance | 0.8 Da |
| Use Average Precursor | False |
| Use Average Fragment | False |
| 4. Ion Series | |
| Use Neutral Loss a Ions | True |
| Use Neutral Loss b Ions | True |

TABLE 10-continued

| Use Neutral Loss y Ions | True |
|---|---|
| Weight of a Ions | 0 |
| Weight of b Ions | 1 |
| Weight of c Ions | 0 |
| Weight of x Ions | 0 |
| Weight of y Ions | 1 |
| Weight of z Ions | 0 |
| 5. Dynamic Modifications | |
| N-Terminal Modification | None |
| C-Terminal Modification | None |
| 1. Dynamic Modification | None |
| 2. Dynamic Modification | None |
| 3. Dynamic Modification | None |
| 4. Dynamic Modification | None |
| 5. Dynamic Modification | None |
| 6. Dynamic Modification | None |
| 6. Static Modifications | |
| Peptide N-Terminus | None |
| Peptide C-Terminus | None |

The database for peptide annotation was created from NCBI, Swissprot, and Uniprot. The resulting annotated proteins are provided above in Table 1.

Example 3

Inosine Concentrations in Dogs with Renal Disease

Dog serum was obtained from field samples submitted to IDEXX Reference Laboratories. Dogs were of various breeds and ages. 25 samples with <1.8 mg/dL serum creatinine were assigned to a low creatinine group, and 25 samples with >1.8 mg/dL serum creatinine were assigned to a high creatinine group. Again, high creatinine is associated with renal disease, therefore inosine levels were assessed to determine whether inosine could be a biomarker for reduced kidney function.

Serum samples from a high creatinine and normal creatinine canine populations were analyzed on LC/MS and differentially produced mass features were indentified by informatics as previously described. LC/MS was run for each sample (i.e., dog) individually. SIEVE software (Thermo Scientific, Waltham, Mass.) was used for statistical analysis of the LC/MS data. Raw LC/MS data files were loaded into SIEVE, and peaks were identified. Statistical analysis was performed to compare peaks in low creatinine and high creatinine samples. A differential peak corresponding to inosine was identified. Serum inosine was found to be depleted in 13 out of the 25 dogs with high serum creatinine. The ion intensity for inosine (as measured by LC/MS) is shown in FIG. 1, where "Renal" represents the 13 dogs with high creatinine and inosine depletion, and "Control" represents all 25 dogs with low serum creatinine.

A protocol utilized for initial LC/MS analysis as shown in FIG. 1 follows below: Plasma extraction was performed in a 0.5 mL protein LoBind eppendorf tube. 110 uL of canine serum was precipitated by addition of 200 uL acetonitrile. After vortexing for 10 seconds, and leaving the sample at room temperature for 30 minutes, the precipitate was pelleted by centrifugation at 13,000 rpm for 30 minutes at room temperature using a benchtop centrifuge. The supernatant was then analyzed by LC/MS. SIEVE and R were used to identify molecules present at differential levels (p-value<0.05).

LC method was performed with Solvent A: 0.1% Formic acid in water and Solvent B: 0.1% Formic acid in acetonitrile:

| No | Time | A % | B % | C % | D % | μL/min |
|----|------|-----|-----|-----|-----|--------|
| 1 | 0 | 100 | 0 | 0 | 0 | 300 |
| 2 | 5 | 100 | 0 | 0 | 0 | 300 |
| 3 | 23 | 65 | 35 | 0 | 0 | 300 |
| 4 | 26 | 65 | 35 | 0 | 0 | 300 |
| 5 | 44 | 5 | 95 | 0 | 0 | 300 |
| 6 | 46 | 5 | 95 | 0 | 0 | 300 |
| 7 | 46.5 | 100 | 0 | 0 | 0 | 300 |
| 8 | 60 | 100 | 0 | 0 | 0 | 300 |

Column: Acquity UPLC BEH130 C18 1.7 μM 2.1 id×150 mm length
Guard Column: vanguard BEH 300 $C_{18}$ 1.7 uM
Injection volume: 25 μL
Tray temp: 10° C.
Column oven temp: 45° C.
MS run time: 60 minutes
Divert valve:
　To waste 0-5
　To source 5-55
　To waste 55-60
Mass Spectrometry method was performed according to the following parameters:
MS scan event 1: FTMS; resolution 30000; scan range 100.0-500.0
MS scan event 2: FTMS; resolution 30000; scan range 500.0-2000.0
MS Tune File Values
Source Type: ESI
Capillary Temp (° C.): 250.00
Sheath gas Flow: 24.00
Aux Gas Flow: 13.00
Sweep Gas Flow: 0
Ion Trap MSn AGC Target: 10000
FTMS Injection waveforms: off
FTMS AGC Target: 500000
Source voltage (kV): 4.50
Source current (μa): 100.00
Capillary Voltage (V): 68.28
Tube Lens (V): 130.00
Skimmer Offset (V): 0.00
Multipole RF Amplifier (Vp-p): 550.00
Multipole 00 offset (V): −1.60
Lens 0 Voltage (V): −2.70
Multipole 0 offset (V): −5.80
Lens 1 Voltage (V): −11.00
Gate Lens offset (V): −60.00
Multipole 1 offset (V): −10.50
Front Lens (V): −5.18
FTMS full microscans: 1
FTMS full Max Ion Time (ms): 500
Ion Trap MSn Micro Scans: 3
Ion Trap MSn Max Ion Time: 100

To verify inosine as a biomarker for kidney disease, a complementary study was performed on dogs with X-linked hereditary nephropathy (XLHN). XLHN is caused by a mutation in the gene COL4A5 (see Example 1 for details). These XLHN dogs provided a model of kidney disease that begins as glomerular defect and progresses to tubular failure. Serum and urine samples from four male dog puppies with XLHN (Table 11) were collected at pre-disease, mid-stage, and end-stage disease and analyzed for inosine as described in the Renal LC/MS Assay provided below.

LC/MS Mobile Phases Prep.
　1. Mobile Phase A: to 1 liter of water add 1 ml acetic acid. Mix well.
　2. Mobile Phase B: to 1 liter of Acetonitrile add 1 ml of acetic acid. Mix well.

Internal STD (IS Solution) Prep
　1. Weigh 5 mg deuterated creatinine and 6-Chloropurine riboside into a 20 ml vial.
　2. Add 5 ml of water to dilute. (1 mg/ml solution).
　3. Transfer 5 ml of #2 into a 2 l flask and add 2 l of water to the mark (2.5 ug/ml solution).
　4. Use #3 as internal STD spiking solution.

STD Curve Prep
　1. Weigh 10 mg creatinine and 10 mg inosine into a 2 ml vial and add 10 ml of Water to dissolve (1 mg/ml solution).
　2. Weigh 345 mg of Bovine Serum albumin (BSA) into 5 ml of phosphate buffer saline solution. Mix well. Scale up or down as needed (PBS-BSA Solution).
　3. Transfer 5 ul of 1 mg/ml solution into 990 ul of PBS-BSA solution (5 ug/ml STD point 1)
　4. Make 11 l/l serial dilutions of #3 for STD points, 2, 3, 4, 5, 6, 7, 8,9,10,11 and a blank.

Sample Prep
　1. Thaw serum samples.
　2. Vortex samples for 10 secs then centrifuge at 3000×g at room temperature for 10 min.
　3. Transfer 50 ul of samples and STD curve points into microfuge tubes or 96 well plate.
　4. Add 50 ul of IS solution into each sample.
　5. Add 100 ul of Acetonitrile.
　6. Vortex to mix.
　7. Sonicate for 20 min in water bath.
　8. Centrifuge at 3000×g for 20 min at 25 degrees c.
　9. Filter supernatant into amber vials/96 well plates using 0.4 micron nylon filters.
　10. Analyze samples by LC/MS.

LC/MS METHOD
HPLC Parameters

| Column | 50 × 4.6 XBridge Amide, 3.5 um column |  |  |  |
|--------|-----|-----|-----|-----|
| Flow | 1 ml/min |  |  |  |
| Gradient Step | total time | flow rate (ul/ml) | A % | B % |
| 0 | 0.1 | 1000 | 20 | 80 |
| 1 | 5.0 | 1000 | 100 | 0 |
| 2. | 8.00 | 1000 | 100 | 0 |
| 3. | 8.10 | 1000 | 20 | 80 |
| 4. | 14.00 | 1000 | 20 | 80 |
| Time | 14 min |  |  |  |
| Temperature | ambient |  |  |  |

MS Parameters
Scan Type: MRM
Polarity: Positive
Scan Mode: N/A
Ion Source: Turbo Spray
Resolution Q1: Unit
Resolution Q3: Unit
Intensity Thres.: 0.00 cps
Settling time: 0.000 msec
MR pause: 5.000 msec
MCA: No
Step size: 0.00 amu

| Q1 Mass (amu) | Q3 Mass (amu) | Dwell (msec) | Parameters | Value |
|---|---|---|---|---|
| Inosine | | | | |
| 269.1 | 137.1 | 150.00 | DP | 30 |
| | | | EP | 7 |
| | | | CEP | 8 |
| | | | CE | 17 |
| | | | CXP | 3 |
| CREATININE | | | | |
| 114.20 | 44.2 | 150.00 | DP | 20 |
| | | | EP | 6.30 |
| | | | CEP | 8.34 |
| | | | CE | 35 |
| | | | CXP | 4 |
| DEUTERATED CREATININE | | | | |
| 117.20 | 47.2 | 150.00 | DP | 20 |
| | | | EP | 6.30 |
| | | | CEP | 8.47 |
| | | | CE | 35 |
| | | | CXP | 4 |
| 6-CHLOROPURINE RIBOSIDE | | | | |
| 285.29 | 153.2 | 150.00 | DP | 30 |
| | | | EP | 7 |
| | | | CEP | 8 |
| | | | CE | 17 |
| | | | CXP | 3 |

The inosine concentrations identified as a result of the above analysis are shown in Table 11, where serum inosine and urine inosine are shown in ug/dL, and creatinine is shown in mg/dL. A significant decrease in inosine is reflected in each animal over time as kidney disease progresses. These data confirm the role of inosine as a biomarker for kidney disease and tubular failure.

TABLE 11

Inosine Levels in Dogs with XLHN

| Animal ID | DAY | Serum Inosine | Urine Inosine | Serum Creatinine |
|---|---|---|---|---|
| RASCAL | 0 | 217.03 | 182.16 | 0.34 |
| | 84 | 188.54 | 44.30 | 1.88 |
| | 119 | 37.10 | 25.99 | 3.02 |
| SANTANA | 0 | 288.08 | 167.91 | 0.41 |
| | 56 | 241.82 | 48.45 | 1.17 |
| | 99 | 85.80 | 33.92 | 6.47 |
| STEEL | 0 | 174.74 | 556.90 | 0.35 |
| | 87 | 128.38 | N/D | 1.84 |
| | 147 | 11.25 | 199.25 | 4.01 |
| XELLUS | 0 | 115.96 | 2335.26 | 0.74 |
| | 91 | 59.87 | N/D | 1.88 |
| | 129 | 40.61 | 1640.90 | 4.05 |

Example 4

Renal Disease Progression in XLHN

Patient blood samples were collected from heterozygous female XLHN dogs as described in Example 1. The samples were prepared as described in Example 1 with the exception that all fractions were eluted in 0.1% formic acid in 35% acetonitrile/water, and that the samples were reconstituted in 0.1% formic acid in 3.5% acetonitrile/water.

The samples were then subjected to LC/MS as described in Example 2 above, except that the tray temperature was 10 degrees Celsius and the MS run time was 60 minutes. Table 12 shows the results of LC/MS measurements of five peptides (SEQ ID NO:1 (Apolipoprotein C1); SEQ ID NO:31 (Cystatin A); SEQ ID NO:18 (Fibrinogen a chain); SEQ ID NO:25 (Inter-Alpha Inhibitor H4 (ITIH4)); SEQ ID NO:23 (Kininogen) over time, in four heterozygous female XLHN dogs. In Table 12, "NF" is an abbreviation for "not found" (i.e. below the limit of detection), while "ND" is an abbreviation for "not determined". As the kidney disease progressed, ApoC1 and Inter-Alpha Inhibitor H4 (ITIH4) levels increased, while Fibrinogen alpha levels decreased. Kininogen levels were higher in the XLHN dogs than in the control dogs. Cystatin A levels were higher in at least three out of the four XLHN dogs as compared to the control dogs.

TABLE 12

Peptide Levels During Renal Disease Progression

| Animal ID | Age | Apolipoprotein C1 AA-26 (SEQ ID NO: 1) | Cystatin A KA-17 (SEQ ID NO: 31) | Fibrinogen α chain EV-11 (SEQ ID NO: 18) | Inter-Alpha Inhibitor H4 (ITIH4) GV-22 (SEQ ID NO: 25) | Kininogen EQ-9 (SEQ ID NO: 23) | Serum Creatinine (mg/dl) |
|---|---|---|---|---|---|---|---|
| CONTROL 1 | 3-4 months Old | NF | NF | 4386.5 | 5.9 | NF | ND |
| CONTROL 2 | 3-4 months Old | 20.6 | NF | 3881.7 | 2.2 | NF | ND |
| CONTROL 3 | 3-4 months Old | 17.7 | NF | 2344.1 | 3.6 | NF | ND |
| CONTROL 4 | 3-4 months Old | 22.3 | NF | 3741.2 | 4.3 | NF | ND |
| RASCAL | 0 | 114.4 | 5.2 | 6712.9 | 26.2 | 42.8 | 0.34 |
| RASCAL | 84 | 321.6 | NF | 6819.3 | 92.3 | 66.5 | 1.88 |
| RASCAL | 119 | 247.1 | 2.7 | 3741.2 | 108.1 | 19.4 | 3.02 |
| XELLUS | 0 | 122.8 | NF | 4233.3 | 58.6 | 10.7 | 0.74 |
| XELLUS | 91 | 145.8 | NF | 3144.7 | 53.0 | 1.2 | 1.88 |

TABLE 12-continued

Peptide Levels During Renal Disease Progression

| Animal ID | Age | Apolipoprotein C1 AA-26 (SEQ ID NO: 1) | Cystatin A KA-17 (SEQ ID NO: 31) | Fibrinogen α chain EV-11 (SEQ ID NO: 18) | Inter-Alpha Inhibitor H4 (ITIH4) GV-22 (SEQ ID NO: 25) | Kininogen EQ-9 (SEQ ID NO: 23) | Serum Creatinine (mg/dl) |
|---|---|---|---|---|---|---|---|
| XELLUS | 129 | 218.6 | NF | 2595.7 | 99.0 | 16.4 | 4.05 |
| SANTANA | 0 | 152.6 | 9.8 | 9439.1 | 62.2 | 26.7 | 0.41 |
| SANTANA | 56 | 149.7 | 30.9 | 8811.6 | 76.6 | 31.0 | 1.17 |
| SANTANA | 99 | 202.4 | 28.2 | 7140.7 | 110.9 | 17.6 | 6.46 |
| STEEL | 0 | 110.9 | 5.9 | 12354.8 | 58.4 | 21.3 | 0.35 |
| STEEL | 87 | 210.9 | 12.6 | 8246.6 | 85.0 | 38.3 | 1.84 |
| STEEL | 147 | 305.3 | NF | 6628.9 | 71.4 | 21.5 | 4.01 |

Example 5

Renal-Failure Induced Canine Model

Dogs of mixed breeds and sizes were injected with dichromate, inducing acute renal failure, specifically due to tubular injury. See Ruegg et al., Toxicol Appl Pharmacol. 1987, 90(2):261-7; Pedraza-Chaverrí et al., BMC Nephrology 2005, 6:4; Chiusolo et al., Toxicol Pathol. 2010, 38:338-45. Specifically, dogs were injected with 0.2 mL/kg of potassium dichromate (5 mg/ml). Serum was prepared from blood samples collected at various time points. NGAL (neutrophil gelatinase-associated lipocalin) was assayed with the Dog NGAL ELISA Kit (BioPorto Diagnostics, Gentofte, Denmark) according to the manufacturer's instructions. Inosine concentrations were measured in serum derived from blood samples taken at various times after injection of dichromate. Inosine and creatinine were measured by LC/MS as previously described in the preceding Example (Renal Assay LC/MS).

Figure 2:
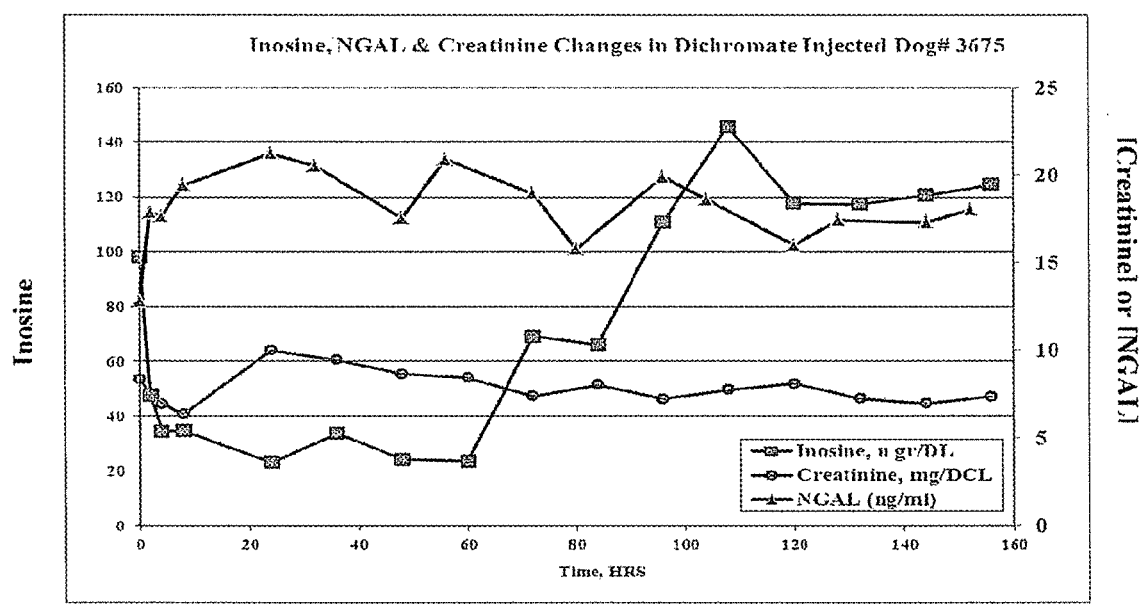
FIG. 2 is a graph representing inosine, NGAL, and creatinine levels over time in an induced canine model of renal disease. Units of measurement include: Inosine in μg/deciliter; Creatinine in mg/centiliter; and NGAL in ng/ml.

A time course of inosine, creatinine and NGAL levels following dichromate injection in a single dog is shown in FIG. 2. Inosine concentrations dropped within 2 hours of dichromate treatment. Between about 60 and 70 hours post-treatment, inosine levels began to recover. See, Fatima, et al., Hum Exp Toxicol 2005, 24:631-8. Creatinine and NGAL were included as reference markers (FIG. 2). In summary, these data illustrate that reduced inosine levels provide a marker for renal failure and tubular injury.

In an additional study, serum samples from dichromate-treated dogs were prepared and subjected to LC/MS as described above in Example 4. FIG. 3 shows time course measurements of the relative concentrations of three peptides (SEQ ID NO:1 (Apolipoprotein C1); SEQ ID NO:23 (Kininogen); SEQ ID NO:25 (Inter-Alpha Inhibitor H4 (ITIH4))) in two dogs.

Figure 3A:
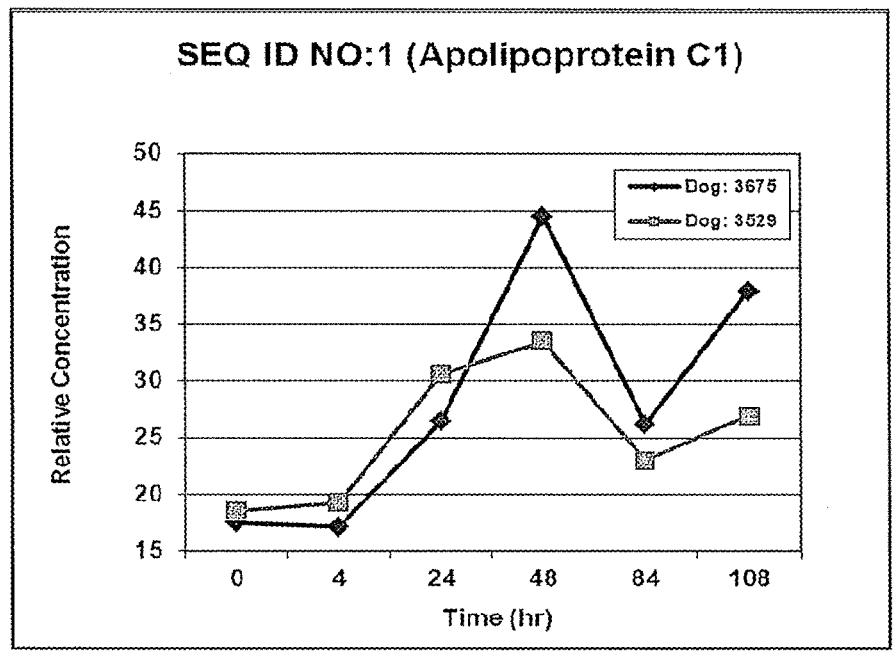
FIG. 3 is a series of graphs representing relative concentrations of apolipoprotein C1 (FIG. 3A), kininogen (FIG. 3B), and Inter-Alpha Inhibitor H4 (ITIH4) (FIG. 3C) levels over time in an induced model of canine model of renal disease.

SEQ ID NO:1 (Apolipoprotein C1) levels increased between about 4 hours and about 48 hours of dichromate treatment (FIG. 3A). Between about 84 and 108 hours post-treatment, peptide SEQ ID NO:1 (Apolipoprotein C1) levels began to recover (decrease). These data illustrate that increased SEQ ID NO:1 (Apolipoprotein C1) levels provide a marker for renal failure and tubular injury.

Figure 3B:
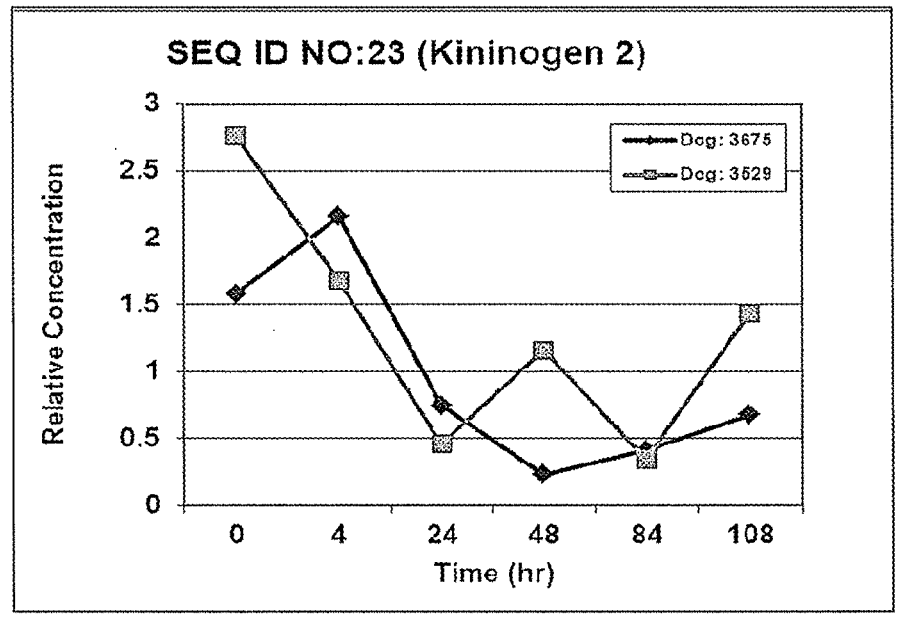

SEQ ID NO:23 (Kininogen) levels generally decreased within the first 1-2 days of dichromate treatment, and recovered (increased) during later time points (FIG. 3B). These data illustrate that decreased SEQ ID NO:23 (Kininogen) levels provide a marker for renal failure and tubular injury.

Figure 3C:
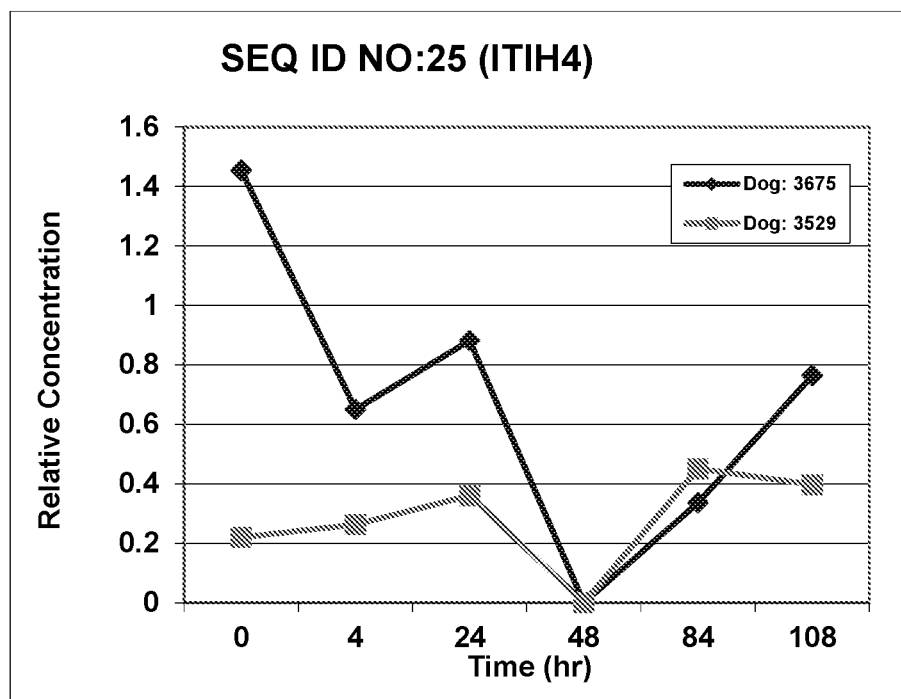

SEQ ID NO:25 (Inter-Alpha Inhibitor H4 (ITIH4)) levels generally decreased by the day 2 of dichromate treatment, and recovered (increased) after day 2 (FIG. 3C). These data illustrate that altered SEQ ID NO:25 (Inter-Alpha Inhibitor H4 (ITIH4)) levels provide a marker for renal failure and tubular injury.

In addition, the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

---

We claim:

1. A method for diagnosis and treatment of kidney disease prior to stage 3 of kidney disease comprising detecting an amount of at least one canine Cystatin A polypeptide selected from the group consisting of full length canine Cystatin A, SEQ ID NO:29, SEQ ID NO:30, SEQ ID NO:31, in a canine patient blood, serum, or plasma sample from a canine patient suspected of suffering from kidney disease; diagnosing the canine patient with kidney disease prior to stage 3 of kidney disease wherein the amount of at least one Cystatin A polypeptide is increased as compared to a control; and treating the canine patient with (i) dialysis; (ii) a diet low in phosphorous and protein; or (iii) dialysis and a diet low in phosphorous and protein.

2. The method of claim 1, wherein the amount of the at least one canine Cystatin A polypeptide is determined by contacting the canine patient sample with one or more antibodies or antigen binding fragments specific for full length canine Cystatin A under conditions suitable for polypeptide/antibody complexes to form and detecting the polypeptide/antibody complexes.

3. The method of claim 2, wherein detecting the amount of polypeptide is performed by an immunoassay selected from the group consisting of an enzyme linked immunosorbent assay (ELISA), western blot, immunofluorescence assay (IFA), radio immunoassay, hemagglutinin assay, fluorescence polarization immunoassay, microtiter plate assays, reversible flow chromatographic binding assay, and immunohistochemistry assay.

4. The method of claim 2, wherein the one or more antibodies or antigen binding fragments are detectably labeled.

5. The method of claim 2, wherein the one or more antibodies or antigen binding fragments are immobilized to a solid support.

6. The method of claim 2, wherein the one or more antibodies or antigen binding fragments are monoclonal antibodies, single chain antibodies, polyclonal antibodies, antigen binding fragments ("Fab fragments"), antigen binding fragments prime, ("Fab' fragments"), antigen binding fragments prime sulfhydryl ("Fab'-SH fragments") fragments, divalent antibody fragments ("F(ab')$_2$ fragments"), or variable domain fragments ("F$_v$ fragments").

7. The method of claim 2, wherein at least one full length canine Cystatin A polypeptide is immobilized on a solid support.

8. The method of claim 1, wherein the amount of the at least one canine Cystatin A polypeptide is determined by liquid chromatography/mass spectrometry.

9. The method of claim 1, wherein the amount of the at least one canine Cystatin A polypeptide is determined by mass spectrometry.

* * * * *

SEQUENCE LISTING

```
<160> NUMBER OF SEQ ID NOS: 59

<210> SEQ ID NO 1
<211> LENGTH: 26
<212> TYPE: PRT
<213> ORGANISM: Canis familiaris

<400> SEQUENCE: 1

Ala Gly Glu Ile Ser Ser Thr Phe Glu Arg Ile Pro Asp Lys Leu Lys
1               5                   10                  15

Glu Phe Gly Asn Thr Leu Glu Asp Lys Ala
            20                  25
```

```
<210> SEQ ID NO 2
<211> LENGTH: 24
<212> TYPE: PRT
<213> ORGANISM: Canis familiaris

<400> SEQUENCE: 2

Glu Ile Ser Ser Thr Phe Glu Arg Ile Pro Asp Lys Leu Lys Glu Phe
1               5                   10                  15

Gly Asn Thr Leu Glu Asp Lys Ala
            20

<210> SEQ ID NO 3
<211> LENGTH: 14
<212> TYPE: PRT
<213> ORGANISM: Canis familiaris

<400> SEQUENCE: 3

Asp Lys Leu Lys Glu Phe Gly Asn Thr Leu Glu Asp Lys Ala
1               5                   10

<210> SEQ ID NO 4
<211> LENGTH: 36
<212> TYPE: PRT
<213> ORGANISM: Canis familiaris

<400> SEQUENCE: 4

Ile Met Gly Ser Asp Ser Asp Ile Phe Thr Asn Ile Gly Thr Pro Glu
1               5                   10                  15

Phe Pro Ser Ser Gly Lys Thr Ser Ser His Ser Lys Gln Phe Val Thr
            20                  25                  30

Ser Ser Thr Thr
        35

<210> SEQ ID NO 5
<211> LENGTH: 28
<212> TYPE: PRT
<213> ORGANISM: Canis familiaris

<400> SEQUENCE: 5

Thr His Ile Met Gly Ser Asp Ser Asp Ile Phe Thr Asn Ile Gly Thr
1               5                   10                  15

Pro Glu Phe Pro Ser Ser Gly Lys Thr Ser Ser His
            20                  25

<210> SEQ ID NO 6
<211> LENGTH: 29
<212> TYPE: PRT
<213> ORGANISM: Canis familiaris

<400> SEQUENCE: 6

Thr His Ile Met Gly Ser Asp Ser Asp Ile Phe Thr Asn Ile Gly Thr
1               5                   10                  15

Pro Glu Phe Pro Ser Ser Gly Lys Thr Ser Ser His Ser
            20                  25

<210> SEQ ID NO 7
<211> LENGTH: 27
<212> TYPE: PRT
<213> ORGANISM: Canis familiaris

<400> SEQUENCE: 7

Ile Met Gly Ser Asp Ser Asp Ile Phe Thr Asn Ile Gly Thr Pro Glu
1               5                   10                  15
```

Phe Pro Ser Ser Gly Lys Thr Ser Ser His Ser
            20                  25

<210> SEQ ID NO 8
<211> LENGTH: 36
<212> TYPE: PRT
<213> ORGANISM: Canis familiaris

<400> SEQUENCE: 8

Ala His Glu Ser Gln Gln Asp Glu Thr Thr Ser Ser Ala Leu Leu Thr
1               5                   10                  15

Gln Met Gln Glu Ser Leu Tyr Ser Tyr Trp Gly Thr Ala Arg Ser Ala
            20                  25                  30

Ala Glu Asp Leu
        35

<210> SEQ ID NO 9
<211> LENGTH: 22
<212> TYPE: PRT
<213> ORGANISM: Canis familiaris

<400> SEQUENCE: 9

Ala His Glu Ser Gln Gln Asp Glu Thr Thr Ser Ser Ala Leu Leu Thr
1               5                   10                  15

Gln Met Gln Glu Ser Leu
            20

<210> SEQ ID NO 10
<211> LENGTH: 29
<212> TYPE: PRT
<213> ORGANISM: Canis familiaris

<400> SEQUENCE: 10

Ala His Glu Ser Gln Gln Asp Glu Thr Thr Ser Ser Ala Leu Leu Thr
1               5                   10                  15

Gln Met Gln Glu Ser Leu Tyr Ser Tyr Trp Gly Thr Ala
            20                  25

<210> SEQ ID NO 11
<211> LENGTH: 22
<212> TYPE: PRT
<213> ORGANISM: Canis familiaris

<400> SEQUENCE: 11

Ala His Glu Ser Gln Gln Asp Glu Thr Thr Ser Ser Ala Leu Leu Thr
1               5                   10                  15

Gln Met Gln Glu Ser Leu
            20

<210> SEQ ID NO 12
<211> LENGTH: 29
<212> TYPE: PRT
<213> ORGANISM: Canis familiaris

<400> SEQUENCE: 12

Ala His Glu Ser Gln Gln Asp Glu Thr Thr Ser Ser Ala Leu Leu Thr
1               5                   10                  15

Gln Met Gln Glu Ser Leu Tyr Ser Tyr Trp Gly Thr Ala
            20                  25

<210> SEQ ID NO 13

```
<211> LENGTH: 15
<212> TYPE: PRT
<213> ORGANISM: Canis familiaris

<400> SEQUENCE: 13

Ala His Glu Ser Gln Gln Asp Glu Thr Thr Ser Ser Ala Leu Leu
1               5                   10                  15

<210> SEQ ID NO 14
<211> LENGTH: 14
<212> TYPE: PRT
<213> ORGANISM: Canis familiaris

<400> SEQUENCE: 14

Asn Ser Lys Glu Gly Glu Phe Ile Ala Glu Gly Gly Gly Val
1               5                   10

<210> SEQ ID NO 15
<211> LENGTH: 13
<212> TYPE: PRT
<213> ORGANISM: Canis familiaris

<400> SEQUENCE: 15

Ser Lys Glu Gly Glu Phe Ile Ala Glu Gly Gly Gly Val
1               5                   10

<210> SEQ ID NO 16
<211> LENGTH: 15
<212> TYPE: PRT
<213> ORGANISM: Canis familiaris

<400> SEQUENCE: 16

Thr Asn Ser Lys Glu Gly Glu Phe Ile Ala Glu Gly Gly Gly Val
1               5                   10                  15

<210> SEQ ID NO 17
<211> LENGTH: 12
<212> TYPE: PRT
<213> ORGANISM: Canis familiaris

<400> SEQUENCE: 17

Lys Glu Gly Glu Phe Ile Ala Glu Gly Gly Gly Val
1               5                   10

<210> SEQ ID NO 18
<211> LENGTH: 11
<212> TYPE: PRT
<213> ORGANISM: Canis familiaris

<400> SEQUENCE: 18

Glu Gly Glu Phe Ile Ala Glu Gly Gly Gly Val
1               5                   10

<210> SEQ ID NO 19
<211> LENGTH: 10
<212> TYPE: PRT
<213> ORGANISM: Canis familiaris

<400> SEQUENCE: 19

Gly Glu Phe Ile Ala Glu Gly Gly Gly Val
1               5                   10

<210> SEQ ID NO 20
<211> LENGTH: 8
<212> TYPE: PRT
```

<213> ORGANISM: Canis familiaris

<400> SEQUENCE: 20

Phe Ile Ala Glu Gly Gly Val
1               5

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

His Gly Gly Gln Arg Glu Leu Asp Phe Asp Leu Glu His Gln
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Asp Glu Glu Trp Asp Ser Gly Lys Glu Gln Gly Pro Thr His Gly His
1               5                   10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Glu Leu Asp Phe Asp Leu Glu His Gln
1               5

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Asp Cys Asp Tyr Lys Glu Ser Thr Gln Ala Ala Thr Gly Glu Cys
1               5                   10                  15

<210> SEQ ID NO 25
<211> LENGTH: 22
<212> TYPE: PRT
<213> ORGANISM: Artificial Sequence
<220> FEATURE:
<223> OTHER INFORMATION: Synthetic

<400> SEQUENCE: 25

Gly Ser Glu Ile Val Val Gly Lys Leu Arg Asp Gln Ser Pro Asp
1               5                   10                  15

Val Leu Ser Ala Lys Val
                20

<210> SEQ ID NO 26

```
<211> LENGTH: 17
<212> TYPE: PRT
<213> ORGANISM: Artificial Sequence
<220> FEATURE:
<223> OTHER INFORMATION: Synthetic

<400> SEQUENCE: 26

Pro Arg Asp Trp Lys Pro Leu Leu Val Pro Ala Ser Pro Glu Asn Val
1               5                   10                  15

Asp

<210> SEQ ID NO 27
<211> LENGTH: 21
<212> TYPE: PRT
<213> ORGANISM: Artificial Sequence
<220> FEATURE:
<223> OTHER INFORMATION: Synthetic

<400> SEQUENCE: 27

Glu Thr Leu Phe Ser Met Met Pro Gly Leu Asn Met Thr Met Asp Lys
1               5                   10                  15

Thr Gly Leu Leu Leu
            20

<210> SEQ ID NO 28
<211> LENGTH: 5
<212> TYPE: PRT
<213> ORGANISM: Artificial Sequence
<220> FEATURE:
<223> OTHER INFORMATION: Synthetic

<400> SEQUENCE: 28

Ala Glu Thr Val Gln
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic

<400> SEQUENCE: 29

Val Gly Asp Asn Ser Tyr Ile His Leu Lys Ile Phe Lys Gly Leu Pro
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Synthetic

<400> SEQUENCE: 30

Leu Thr Leu Thr Gly Tyr Gln Thr Asp Lys Ser Lys Asp Asp Glu Leu
1               5                   10                  15

Thr Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31
```

Lys Pro Gln Leu Glu Glu Lys Thr Asn Glu Thr Tyr Gln Glu Phe Glu
1               5                   10                  15

Ala

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Tyr Gln Thr Asn Lys Ala Lys His Asp Glu Leu Ala Tyr Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic

<400> SEQUENCE: 33

Gln Thr Asn Lys Ala Lys His Asp Glu Leu Ala Tyr Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Glu Asn Lys Pro Leu Ala Leu Ser Ser Tyr Gln Thr Asn Lys
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Gln Val Val Ala Gly Thr Pro Tyr
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Glu Glu Arg Glu Asn Lys Lys Tyr Thr Thr Phe Lys
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic -continued

<400> SEQUENCE: 37

Tyr Phe Ile Lys Val Gln Val Asp Asp Glu Phe Val His Leu Arg
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic

<400> SEQUENCE: 38

Val Val Ala Gly Thr Pro Tyr Phe Ile Lys Val Gln Val Asp Asp Asp
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Met Gln Asn Leu Asn Asp Arg Leu Ala Ser
1               5                   10

<210> SEQ ID NO 40
<211> LENGTH: 22
<212> TYPE: PRT
<213> ORGANISM: Artificial Sequence
<220> FEATURE:
<223> OTHER INFORMATION: Synthetic

<400> SEQUENCE: 40

Phe Gly Gly Gly Tyr Gly Gly Val Ser Phe Gly Gly Ser Phe Gly
1               5                   10                  15

Gly Gly Ser Phe Gly Gly
            20

<210> SEQ ID NO 41
<211> LENGTH: 12
<212> TYPE: PRT
<213> ORGANISM: Artificial Sequence
<220> FEATURE:
<223> OTHER INFORMATION: Synthetic

<400> SEQUENCE: 41

Ser Phe Gly Gly Gly Tyr Gly Gly Val Ser Phe Gly
1               5                   10

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Phe Ser Arg Gly Ser Ser Gly Gly Gly Cys Phe Gly Gly Ser Ser Gly
1               5                   10                  15

Gly Tyr Gly Gly Leu Gly Gly
            20

<210> SEQ ID NO 43
<211> LENGTH: 5

<212> TYPE: PRT
<213> ORGANISM: Artificial Sequence
<220> FEATURE:
<223> OTHER INFORMATION: Synthetic

<400> SEQUENCE: 43

Glu Glu Gln Leu Gln
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

Gln Asn Arg Lys Asp Ala Glu Ala Trp Phe Asn Glu Lys Ser Lys
1               5                   10                  15

<210> SEQ ID NO 45
<211> LENGTH: 18
<212> TYPE: PRT
<213> ORGANISM: Artificial Sequence
<220> FEATURE:
<223> OTHER INFORMATION: Synthetic

<400> SEQUENCE: 45

Pro Arg Asp Tyr Ser Lys Tyr Tyr Gln Thr Ile Glu Asp Leu Lys Asn
1               5                   10                  15

Gln Ile

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Lys Asp Ala Glu Ala Trp Phe Asn Glu Lys Ser Lys Glu Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Lys Tyr Glu Asn Glu Val Ala Leu Arg Gln Ser Val Glu Ala
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Synthetic

<400> SEQUENCE: 48

Lys Ser Lys Glu Leu Thr Thr Glu Ile Asn Ser Asn Ile Glu Gln Met
1               5                   10                  15

<210> SEQ ID NO 49

```
<211> LENGTH: 5
<212> TYPE: PRT
<213> ORGANISM: Artificial Sequence
<220> FEATURE:
<223> OTHER INFORMATION: Synthetic

<400> SEQUENCE: 49

Leu Gln Ile Asp Asn
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic

<400> SEQUENCE: 50

Ser Ile Gly Gly Gly Phe Ser Ser Gly Gly
1               5                   10

<210> SEQ ID NO 51
<211> LENGTH: 25
<212> TYPE: PRT
<213> ORGANISM: Artificial Sequence
<220> FEATURE:
<223> OTHER INFORMATION: Synthetic

<400> SEQUENCE: 51

Phe Gly Gly Gly Gly Phe Ser Gly Gly Ser Phe Gly Gly Tyr Gly Gly
1               5                   10                  15

Gly Tyr Gly Gly Asp Gly Gly Leu Leu
            20                  25

<210> SEQ ID NO 52
<211> LENGTH: 16
<212> TYPE: PRT
<213> ORGANISM: Artificial Sequence
<220> FEATURE:
<223> OTHER INFORMATION: Synthetic

<400> SEQUENCE: 52

Leu Glu Asn Glu Ile Gln Thr Tyr Arg Ser Leu Leu Glu Gly Glu Gly
1               5                   10                  15

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Gly Ser Ile Gly Gly Gly Phe Ser Ser Gly
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic

<400> SEQUENCE: 54

Glu Asp Leu Lys Asn Gln Ile Leu Asn Leu Thr Thr Asp Asn
1               5                   10
```

```
<210> SEQ ID NO 55
<211> LENGTH: 22
<212> TYPE: PRT
<213> ORGANISM: Artificial Sequence
<220> FEATURE:
<223> OTHER INFORMATION: Synthetic

<400> SEQUENCE: 55

Gly Gly Gly Gly Tyr Gly Gly Gly Ser Ser Gly Gly Gly Gly Ser His
1               5                   10                  15

Gly Gly Ser Ser Gly Gly
            20

<210> SEQ ID NO 56
<211> LENGTH: 16
<212> TYPE: PRT
<213> ORGANISM: Artificial Sequence
<220> FEATURE:
<223> OTHER INFORMATION: Synthetic

<400> SEQUENCE: 56

Gly Arg Tyr Cys Val Gln Leu Ser Gln Ile Gln Ala Gln Ile Ser Ser
1               5                   10                  15

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Arg Val Leu Asp Glu Leu Thr Leu Thr
1               5

<210> SEQ ID NO 58
<211> LENGTH: 17
<212> TYPE: PRT
<213> ORGANISM: Artificial Sequence
<220> FEATURE:
<223> OTHER INFORMATION: Synthetic

<400> SEQUENCE: 58

Arg Leu Ala Ser Tyr Leu Asp Lys Val Arg Ala Leu Glu Glu Ser Asn
1               5                   10                  15

Tyr

<210> SEQ ID NO 59
<211> LENGTH: 17
<212> TYPE: PRT
<213> ORGANISM: Artificial Sequence
<220> FEATURE:
<223> OTHER INFORMATION: Synthetic

<400> SEQUENCE: 59

Gly Gly Gly Tyr Gly Gly Asp Gly Gly Leu Leu Ser Gly Asn Glu Lys
1               5                   10                  15

Val
```